United States Patent
David

(10) Patent No.: US 9,573,242 B2
(45) Date of Patent: *Feb. 21, 2017

(54) COMPUTER PROGRAM PRODUCT AND METHOD OF CONTROLLING POLISHING OF A SUBSTRATE

(71) Applicant: Applied Materials, Inc., Santa Clara, CA (US)

(72) Inventor: Jeffrey Drue David, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 14/299,728

(22) Filed: Jun. 9, 2014

(65) Prior Publication Data

US 2015/0024659 A1   Jan. 22, 2015

Related U.S. Application Data

(63) Continuation of application No. 13/094,677, filed on Apr. 26, 2011, now Pat. No. 8,747,189.

(51) Int. Cl.
*B24B 37/013* (2012.01)
*B24B 37/005* (2012.01)
(Continued)

(52) U.S. Cl.
CPC .......... *B24B 37/013* (2013.01); *B24B 37/005* (2013.01); *B24B 37/042* (2013.01);
(Continued)

(58) Field of Classification Search
CPC ..... B24B 37/013; B24B 37/005; B24B 49/04; B24B 37/042; B24B 37/105; B24B 49/12; H01L 21/304; H01L 21/3212; G05B 15/02; G01B 11/0683; G01J 3/28; G01N 2021/8438; G01N 2021/8416; G01N 21/55; G01N 21/9501
See application file for complete search history.

(56) References Cited

U.S. PATENT DOCUMENTS 6,309,276 B1 * 10/2001 Tsai ...................... B24B 37/013
  451/41
6,361,646 B1   3/2002 Bibby et al.
(Continued)

*Primary Examiner* — Ramesh Patel
(74) *Attorney, Agent, or Firm* — Fish & Richardson P.C.

(57) ABSTRACT

A method of controlling polishing includes polishing a substrate of a non-metallic layer undergoing polishing and a metal layer underlying the non-metallic layer; storing a metal reference spectrum, the metal reference spectrum being a spectrum of light reflected from a same metal material as the metal layer; measuring a sequence of raw spectra of light reflected from the substrate during polishing with an in-situ optical monitoring system; normalizing each raw spectrum in the sequence of spectra to generate a sequence of normalized spectra, of which normalizing includes a division operation where the measured spectrum is in the numerator and the metal reference spectrum is in the denominator; and determining at least one of a polishing endpoint or an adjustment for a polishing rate based on at least one normalized predetermined spectrum from the sequence of normalized spectra.

18 Claims, 14 Drawing Sheets

(51) Int. Cl.
*H01L 21/304* (2006.01)
*B24B 49/12* (2006.01)
*B24B 49/04* (2006.01)
*G05B 15/02* (2006.01)
*B24B 37/04* (2012.01)
*B24B 37/10* (2012.01)
*G01B 11/06* (2006.01)
*G01J 3/28* (2006.01)
*G01N 21/55* (2014.01)
*G01N 21/95* (2006.01)
*G01N 21/84* (2006.01)
*H01L 21/321* (2006.01)

(52) U.S. Cl.
CPC ............ *B24B 37/105* (2013.01); *B24B 49/04* (2013.01); *B24B 49/12* (2013.01); *G01B 11/0683* (2013.01); *G05B 15/02* (2013.01); *H01L 21/304* (2013.01); *G01J 3/28* (2013.01); *G01N 21/55* (2013.01); *G01N 21/9501* (2013.01); *G01N 2021/8416* (2013.01); *G01N 2021/8438* (2013.01); *H01L 21/3212* (2013.01)

(56) References Cited

U.S. PATENT DOCUMENTS

| | | | | |
|---|---|---|---|---|
| 6,476,921 B1* | 11/2002 | Saka | ................... | B24B 37/013 356/630 |
| 6,910,942 B1* | 6/2005 | Dornfeld | .............. | B24B 37/013 451/285 |
| 6,991,514 B1* | 1/2006 | Meloni | ................... | B24B 49/12 451/288 |
| 7,008,295 B2* | 3/2006 | Wiswesser | .............. | B24B 49/12 451/285 |
| 7,052,365 B2* | 5/2006 | Dornfeld | .............. | B24B 37/013 451/285 |
| 7,670,206 B2* | 3/2010 | Togawa | ................ | B24B 37/013 324/229 |
| 8,088,298 B2* | 1/2012 | Swedek | ................ | B24B 37/013 216/84 |
| 8,747,189 B2* | 6/2014 | David | ................... | B24B 37/013 156/345.12 |
| 8,814,631 B2* | 8/2014 | David | ................... | B24B 37/013 451/41 |
| 8,944,884 B2* | 2/2015 | David | ................... | B24B 37/013 451/11 |
| 8,977,379 B2* | 3/2015 | David | ................... | B24B 37/013 700/121 |
| 9,352,440 B2* | 5/2016 | David | ..................... | B24B 49/12 |
| 9,362,186 B2* | 6/2016 | Kitajima | ................ | H01L 22/26 |
| 2007/0042675 A1* | 2/2007 | Benvegnu | ............. | B24B 37/013 451/5 |
| 2012/0034845 A1* | 2/2012 | Hu | ........................ | B24B 37/013 451/5 |
| 2012/0268738 A1* | 10/2012 | David | ................... | B24B 37/013 356/326 |
| 2012/0274932 A1* | 11/2012 | David | ................... | B24B 37/013 356/300 |
| 2015/0314415 A1* | 11/2015 | David | ................... | B24B 37/013 451/6 |
| 2016/0018815 A1* | 1/2016 | Kitajima | .............. | G05B 19/418 700/121 |
| 2016/0020157 A1* | 1/2016 | Kitajima | ................ | H01L 22/26 438/10 |

* cited by examiner

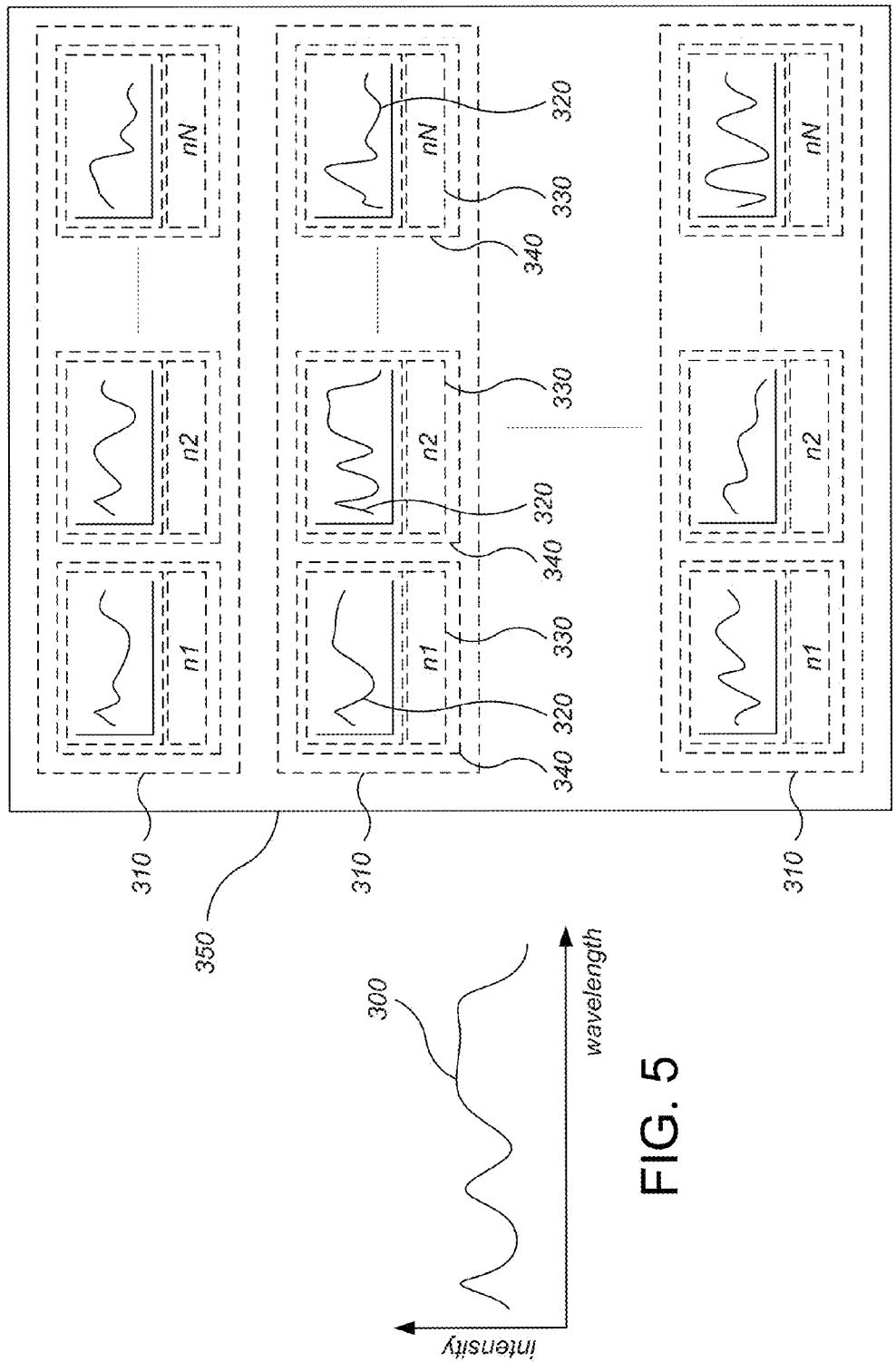

COMPUTER PROGRAM PRODUCT AND METHOD OF CONTROLLING POLISHING OF A SUBSTRATE

CROSS REFERENCE TO RELATED APPLICATIONS

This application is a continuation of and claims priority to U.S. patent application Ser. No. 13/094,677, filed on Apr. 26, 2011, now U.S. Pat. No. 8,747,189, the entire contents of which are hereby incorporated by reference.

TECHNICAL FIELD

The present disclosure relates to polishing control methods, e.g., during chemical mechanical polishing of substrates.

BACKGROUND

An integrated circuit is typically formed on a substrate by the sequential deposition of conductive, semiconductive, or insulative layers on a silicon wafer. One fabrication step involves depositing a filler layer over a non-planar surface and planarizing the filler layer. For certain applications, the filler layer is planarized until the top surface of a patterned layer is exposed. A conductive filler layer, for example, can be deposited on a patterned insulative layer to fill the trenches or holes in the insulative layer. After planarization, the portions of the conductive layer remaining between the raised pattern of the insulative layer form vias, plugs, and lines that provide conductive paths between thin film circuits on the substrate. For other applications, such as oxide polishing, the filler layer is planarized until a predetermined thickness is left over the non planar surface. In addition, planarization of the substrate surface is usually required for photolithography.

Chemical mechanical polishing (CMP) is one accepted method of planarization. This planarization method typically requires that the substrate be mounted on a carrier head. The exposed surface of the substrate is typically placed against a rotating polishing pad. The carrier head provides a controllable load on the substrate to push it against the polishing pad. A polishing liquid, such as a slurry with abrasive particles, is typically supplied to the surface of the polishing pad.

One problem in CMP is determining whether the polishing process is complete, i.e., whether a substrate layer has been planarized to a desired flatness or thickness, or when a desired amount of material has been removed. Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, it may not be possible to determine the polishing endpoint merely as a function of polishing time.

In some systems, a substrate is optically monitored in-situ during polishing, e.g., through a window in the polishing pad. However, existing optical monitoring techniques may not satisfy increasing demands of semiconductor device manufacturers.

SUMMARY

In some optical monitoring processes, a spectrum measured in-situ, e.g., during a polishing process of CMP, is compared to a library of reference spectra to find the best matching reference spectrum. However, the spectrum measured in-situ usually contains multiple noise components that can distort the results, rendering inaccurate comparison to the library of reference spectra. One of the most prominent noise components is underlayer variation that can be stacked with different materials of different indices of refraction, thickness and other spectrum related properties. This problem is accentuated during back end of line (BEOL) processes, in which silicon background substrate does not provide a good base spectrum signal for obtaining the normalized reflectance spectra. If silicon is used for normalization, then there would be significant copper (or other deposited conductive material) noise left in the spectrum signal. Similar problem is even more important in model based techniques which require correct substrate when stack is built. Therefore an improved polishing/normalization method with a different spectrum characteristic (e.g. by using a copper background substrate) is disclosed here to improve the measured spectra in comparison to the library of reference spectra.

In one aspect a method of controlling polishing includes polishing a substrate. The substrate includes a non-metallic layer undergoing polishing and a metal layer underlying the non-metallic layer. A metal reference spectrum is stored. The metal reference spectrum is a spectrum of light reflected from a same metal material as the metal layer. A sequence of raw spectra of light is reflected from the substrate during polishing with an in-situ optical monitoring system. Each raw spectrum in the sequence of raw spectra is normalized to generate a sequence of normalized spectra. Normalizing includes a division operation in which the raw spectrum is in the numerator and the metal reference spectrum is in the denominator. At least one of a polishing endpoint or an adjustment for a polishing rate is determined based on at least one normalized predetermined spectrum from the sequence of normalized spectra.

Implementations may include one or more of the following features. One or more dark spectra may be stored. The one or more dark spectra may be spectra measured by the in-situ optical monitoring system when no substrate is being measured by the in-situ optical monitoring system. Normalizing may include subtracting the one or more dark spectra from the raw spectrum and the metal reference spectrum. Normalizing may include calculating $R=(A-DA)/(B-DB)$ where R is the normalized spectrum, A is the raw spectrum, B is the metal reference spectrum and DA and DB are dark spectra. DA and DB may be the same dark spectrum. DA and DB may be different dark spectra. DA may be a dark spectrum collected when the raw spectrum is collected and DB may be a dark spectrum collected when the base layer reference spectrum is collected. DA may be a dark spectrum collected at the same platen rotation as the raw spectrum and DB may be a dark spectrum collected at the same platen rotation as the base layer reference spectrum. The metal reference spectrum may be generated. Generating the metal reference spectrum may include measuring a spectrum of light reflected from the metal material with the in-situ optical monitoring system. Measuring a spectrum of light reflected from the metal material may include polishing a blanket copper wafer. Generating the metal reference spectrum may include calculating the metal reference spectrum from an optical model. The metal layer may consist of copper, aluminum or tungsten. A sequence of values may be generated from the sequence of normalized spectra, a function may be fit to the sequence of values, a projected time at which the function reaches a target value may be determined, and at least one of a polishing endpoint or an adjustment for a polishing rate may be determined based on the projected time. For each normalized spectrum from the sequence of normalized spectra, a best matching reference spectrum may be found from a library having a plurality of reference spectra. Generating the sequence of values may include, for each best matching reference spectrum, determining a value associated the best matching reference spectrum. For each normalized spectrum from the sequence of normalized spectra, a position or width of a peak or valley of the normalized spectrum may be found to generate a sequence of position or width values, and the sequence of values may be generated from the sequence of position or width values. Polishing may be halted when the function matches or exceeds a target value. The substrate may include a plurality of zones, and a polishing rate of each zone may be independently controllable by an independently variable polishing parameter. For each zone, a sequence of normalized spectra may be generated and a sequence of values may be generated from the sequence of normalized spectra. Based on the sequence of values for each zone, the polishing parameter for at least one zone may be adjusted to adjust the polishing rate of the at least one zone such that the plurality of zones have a smaller difference in thickness at the polishing endpoint than without such adjustment. Polishing the substrate may be a back-end-of-line portion of an integrated circuit fabrication process.

In another aspect, a computer program product, tangibly embodied in a machine readable storage device, includes instructions to carry out the method.

Implementations may optionally include one or more of the following advantages. A raw spectrum can be normalized to remove variations from a metal underlayer, thus improving the quality of the measured spectrum used for the endpoint detection algorithm. Thus, reliability of the endpoint system to detect a desired polishing endpoint can be improved, and within-wafer and wafer-to-wafer thickness non-uniformity (WIWNU and WTWNU) can be reduced.

BRIEF DESCRIPTION OF THE DRAWINGS

FIG. 5 illustrates a measured spectrum from the in-situ optical monitoring system.

FIG. 6 illustrates a library of reference spectra.

Like reference numbers and designations in the various drawings indicate like elements.

DETAILED DESCRIPTION

One optical monitoring technique is to measure spectra of light reflected from a substrate during polishing, and identify a matching reference spectra from a library. In some implementations, the matching reference spectra provide a series of index values, and a function, e.g., a line, is fit to the series of index values. The projection of the function to a target value can be used to determine endpoint or to change a polishing rate.

One potential problem, is that the spectrum measured in-situ usually contains multiple noise components that can distort the results, rendering inaccurate comparison to the library of reference spectra. One of the most prominent noise components is underlayer variation that can be stacked with different materials of different indices of refraction, thickness and other spectrum related properties. This problem is accentuated during back end of line (BEOL) processes, in which silicon background substrate does not provide a good base spectrum signal for obtaining the normalized reflectance spectra. If silicon is used for normalization, then there would be significant copper (or other deposited conductive material) noise left in the spectrum signal. Similar problem is even more important in model based techniques which require correct substrate when stack is built. However, it is possible to reduce or avoid this problem by using a copper substrate and its reflectance spectrum to reduce noise and improve the spectra measurement accuracy.

A substrate can include a first layer and a second layer disposed over the second layer. The first layer can be a dielectric. Both the first layer and the second layer are at least semi-transparent. Together, the first layer and one or more additional layers (if present) provide a layer stack below the second layer.

Figure 1A:
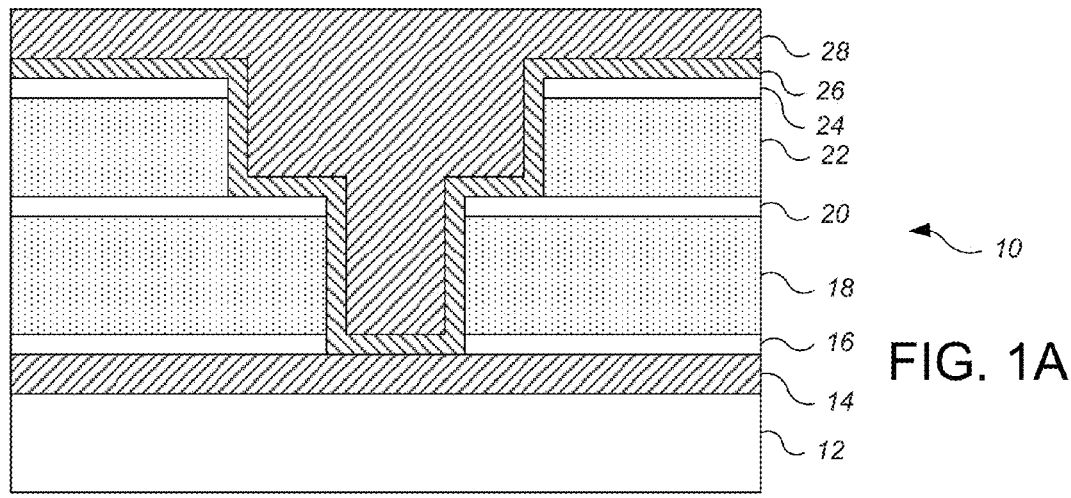
FIG. 1A-1C are schematic cross-sectional views of a substrate before, during and after polishing.

As an example, referring to FIG. 1A, a substrate 10 can include a base structure 12, e.g., a glass sheet or semiconductor wafer, possibility with further layers of conductive or insulating material. A conductive layer 14, e.g., a metal, such as copper, tungsten or aluminum, is disposed over the base structure 12. A patterned lower first dielectric layer 18 is disposed over the conductive layer 14, and a patterned upper second dielectric layer 22 is disposed over the lower dielectric layer 18. The lower dielectric layer 18 and the upper dielectric layer 22 can be an insulator, e.g., an oxide, such as silicon dioxide, or a low-k material, such as carbon doped silicon dioxide, e.g., Black Diamond™ (from Applied Materials, Inc.) or Coral™ (from Novellus Systems, Inc.). The lower dielectric layer 18 and the upper dielectric layer 22 can be composed of the same material or different materials.

Optionally disposed between the conductive layer 14 and the lower dielectric layer 18 is a passivation layer 16, e.g., silicon nitride. Optionally disposed between the lower dielectric layer 18 and the upper dielectric layer 22 is a etch stop layer 20, e.g., a dielectric material, e.g., silicon carbide, silicon nitride, or carbon-silicon nitride (SiCN). Disposed over the upper dielectric layer 22 and at least into the trenches in the upper dielectric layer 22 is a barrier layer 26 of different composition than the lower dielectric layer 18 and the upper dielectric layer 22. For example, the barrier layer 26 can be a metal or a metal nitride, e.g., tantalum nitride or titanium nitride. Optionally disposed between the upper dielectric layer 22 and the barrier layer 26 first layer and the second layer are one or more additional layers 24 of another dielectric material different from the second dielectric material, e.g., a low-k capping material, e.g., a material formed from tetraethyl orthosilicate (TEOS). Disposed over the upper dielectric layer 22 (and at least in trenches provided by the pattern of the upper dielectric layer 22) is a conductive material 28, e.g., a metal, such as copper, tungsten or aluminum.

The layers between the conductive layer 14 and the conductive material 28, including the barrier layer 26, can have a sufficiently low extinction coefficient and/or be sufficiently thin that they transmits light from the optical monitoring system. In contrast, the conductive layer 14 and the conductive material 28 can be sufficiently thick and have a sufficiently high extinction coefficient to be opaque to light from the optical monitoring system.

In some implementations, the upper dielectric layer 22 provides the first layer, and the barrier layer 26 provides the second layer, although other layers are possible for the first layer and the second layer.

Figure 1B:
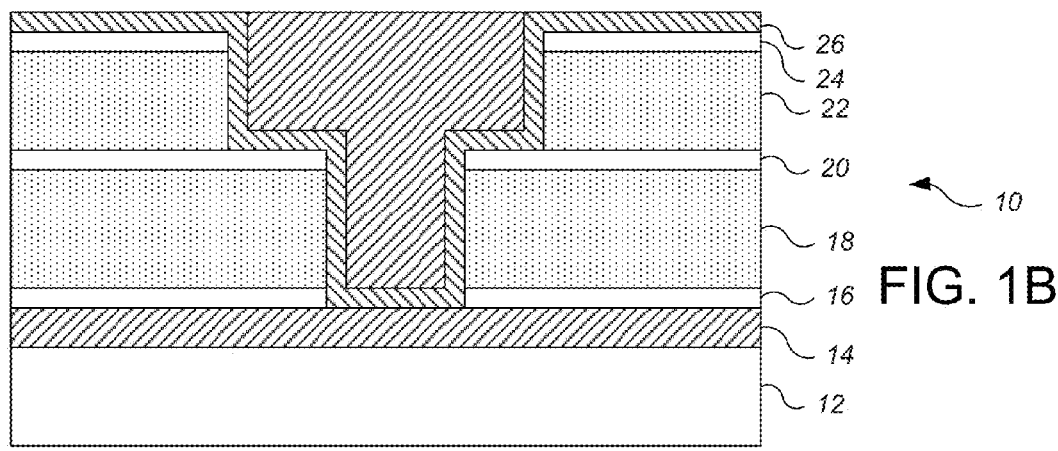
Figure 1C:
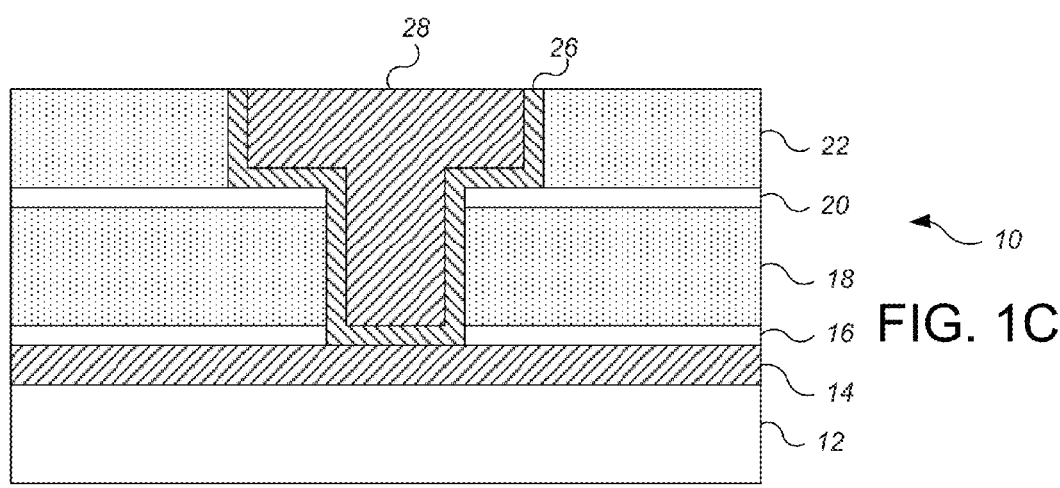

Chemical mechanical polishing can be used to planarize the substrate until the second layer is exposed. For example, as shown in FIG. 1B, initially the opaque conductive material 28 is polished until a non-opaque second layer, e.g., the barrier layer 26 is exposed. Then, referring to FIG. 1C, the portion of the second layer remaining over the first layer is removed and the substrate is polished until the first layer, e.g., the upper dielectric layer 22, is exposed. In addition, it is sometimes desired to polish the first layer, e.g., the dielectric layer 22, until a target thickness remains or a target amount of material has been removed. In the example of FIGS. 1A-1C, after planarization, the portions of the conductive material 28 remaining between the raised pattern of the upper dielectric layer 22 form vias and the like.

One method of polishing is to polish the conductive material 28 on a first polishing pad at least until the second layer, e.g., the barrier layer 26, is exposed. In addition, a portion of the thickness of the second layer can be removed, e.g., during an overpolishing step at the first polishing pad. The substrate is then transferred to a second polishing pad, where the second layer, e.g., the barrier layer 26 is completely removed, and a portion of the thickness of the first layer, e.g., upper dielectric layer 22, such as the low-k dielectric, is also removed. In addition, if present, the additional layer or layers, e.g., the capping layer, between the first and second layer can be removed in the same polishing operation at the second polishing pad.

Figure 2:
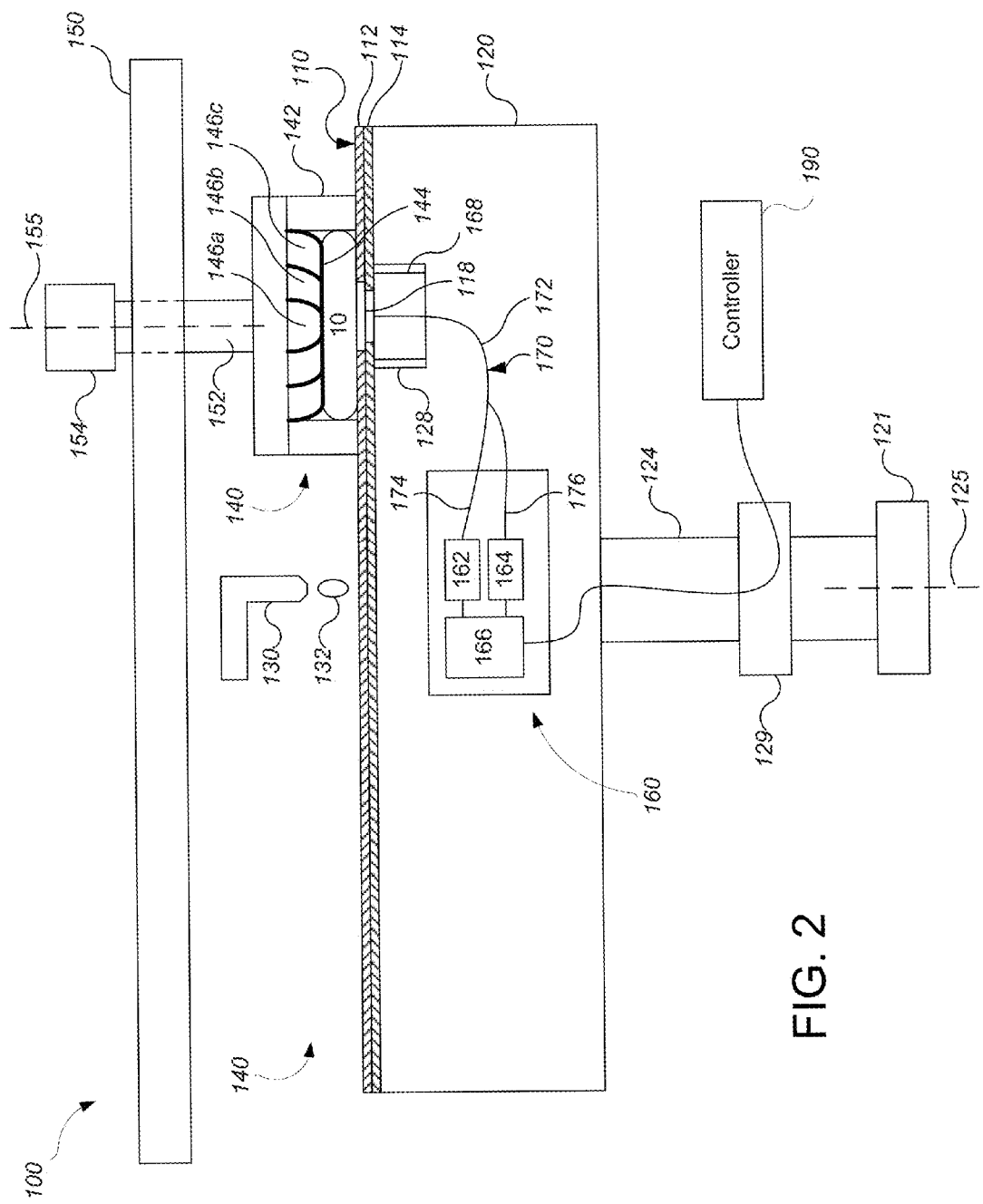
FIG. 2 illustrates a schematic cross-sectional view of an example of a polishing apparatus.

FIG. 2 illustrates an example of a polishing apparatus 100. The polishing apparatus 100 includes a rotatable disk-shaped platen 120 on which a polishing pad 110 is situated. The platen is operable to rotate about an axis 125. For example, a motor 121 can turn a drive shaft 124 to rotate the platen 120. The polishing pad 110 can be a two-layer polishing pad with an outer polishing layer 112 and a softer backing layer 114.

The polishing apparatus 100 can include a port 130 to dispense polishing liquid 132, such as a slurry, onto the polishing pad 110 to the pad. The polishing apparatus can also include a polishing pad conditioner to abrade the polishing pad 110 to maintain the polishing pad 110 in a consistent abrasive state.

The polishing apparatus 100 includes one or more carrier heads 140. Each carrier head 140 is operable to hold a substrate 10 against the polishing pad 110. Each carrier head 140 can have independent control of the polishing parameters, for example pressure, associated with each respective substrate.

Figure 3:
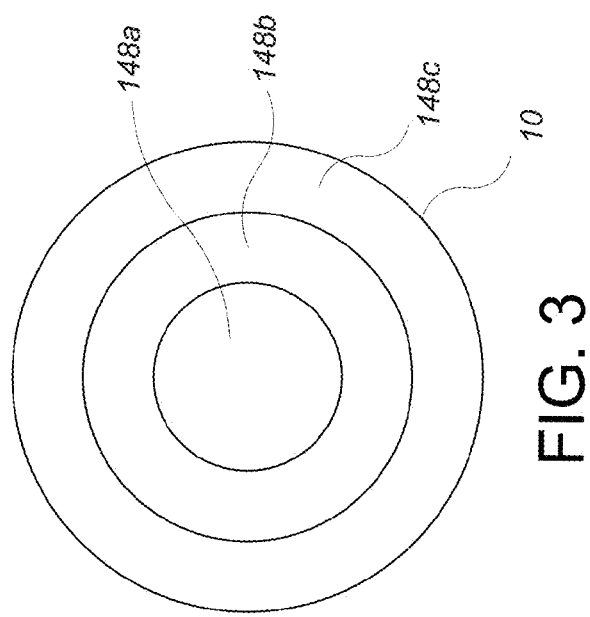
FIG. 3 illustrates a schematic top view of a substrate having multiple zones.

In particular, each carrier head 140 can include a retaining ring 142 to retain the substrate 10 below a flexible membrane 144. Each carrier head 140 also includes a plurality of independently controllable pressurizable chambers defined by the membrane, e.g., three chambers 146a-146c, which can apply independently controllable pressurizes to associated zones 148a-148c on the flexible membrane 144 and thus on the substrate 10 (see FIG. 3). Referring to FIG. 3, the center zone 148a can be substantially circular, and the remaining zones 148b-148c can be concentric annular zones around the center zone 148a. Although only three chambers are illustrated in FIGS. 2 and 3 for ease of illustration, there could be one or two chambers, or four or more chambers, e.g., five chambers.

Returning to FIG. 2, each carrier head 140 is suspended from a support structure 150, e.g., a carousel, and is connected by a drive shaft 152 to a carrier head rotation motor 154 so that the carrier head can rotate about an axis 155. Optionally each carrier head 140 can oscillate laterally, e.g., on sliders on the carousel 150; or by rotational oscillation of the carousel itself. In operation, the platen is rotated about its central axis 125, and each carrier head is rotated about its central axis 155 and translated laterally across the top surface of the polishing pad.

While only one carrier head 140 is shown, more carrier heads can be provided to hold additional substrates so that the surface area of polishing pad 110 may be used efficiently. Thus, the number of carrier head assemblies adapted to hold substrates for a simultaneous polishing process can be based, at least in part, on the surface area of the polishing pad 110.

The polishing apparatus also includes an in-situ optical monitoring system 160, e.g., a spectrographic monitoring system, which can be used to determine whether to adjust a polishing rate or an adjustment for the polishing rate as discussed below. An optical access through the polishing pad is provided by including an aperture (i.e., a hole that runs through the pad) or a solid window 118. The solid window 118 can be secured to the polishing pad 110, e.g., as a plug that fills an aperture in the polishing pad, e.g., is molded to or adhesively secured to the polishing pad, although in some implementations the solid window can be supported on the platen 120 and project into an aperture in the polishing pad.

The optical monitoring system 160 can include a light source 162, a light detector 164, and circuitry 166 for sending and receiving signals between a remote controller 190, e.g., a computer, and the light source 162 and light detector 164. One or more optical fibers can be used to transmit the light from the light source 162 to the optical access in the polishing pad, and to transmit light reflected from the substrate 10 to the detector 164. For example, a bifurcated optical fiber 170 can be used to transmit the light from the light source 162 to the substrate 10 and back to the detector 164. The bifurcated optical fiber an include a trunk 172 positioned in proximity to the optical access, and two branches 174 and 176 connected to the light source 162 and detector 164, respectively.

In some implementations, the top surface of the platen can include a recess 128 into which is fit an optical head 168 that holds one end of the trunk 172 of the bifurcated fiber. The optical head 168 can include a mechanism to adjust the vertical distance between the top of the trunk 172 and the solid window 118.

The output of the circuitry 166 can be a digital electronic signal that passes through a rotary coupler 129, e.g., a slip ring, in the drive shaft 124 to the controller 190 for the optical monitoring system. Similarly, the light source can be turned on or off in response to control commands in digital electronic signals that pass from the controller 190 through the rotary coupler 129 to the optical monitoring system 160. Alternatively, the circuitry 166 could communicate with the controller 190 by a wireless signal.

The light source 162 can be operable to emit white light. In one implementation, the white light emitted includes light having wavelengths of 200-800 nanometers. A suitable light source is a xenon lamp or a xenon mercury lamp.

The light detector 164 can be a spectrometer. A spectrometer is an optical instrument for measuring intensity of light over a portion of the electromagnetic spectrum. A suitable spectrometer is a grating spectrometer. Typical output for a spectrometer is the intensity of the light as a function of wavelength (or frequency).

As noted above, the light source 162 and light detector 164 can be connected to a computing device, e.g., the controller 190, operable to control their operation and receive their signals. The computing device can include a microprocessor situated near the polishing apparatus, e.g., a programmable computer. With respect to control, the computing device can, for example, synchronize activation of the light source with the rotation of the platen 120.

In some implementations, the light source 162 and detector 164 of the in-situ monitoring system 160 are installed in and rotate with the platen 120. In this case, the motion of the platen will cause the sensor to scan across each substrate. In particular, as the platen 120 rotates, the controller 190 can cause the light source 162 to emit a series of flashes starting just before and ending just after the optical access passes below the substrate 10. Alternatively, the computing device can cause the light source 162 to emit light continuously starting just before and ending just after each substrate 10 passes over the optical access. In either case, the signal from the detector can be integrated over a sampling period to generate spectra measurements at a sampling frequency.

In operation, the controller 190 can receive, for example, a signal that carries information describing a spectrum of the light received by the light detector for a particular flash of the light source or time frame of the detector. Thus, this spectrum is a spectrum measured in-situ during polishing.

Figure 4:
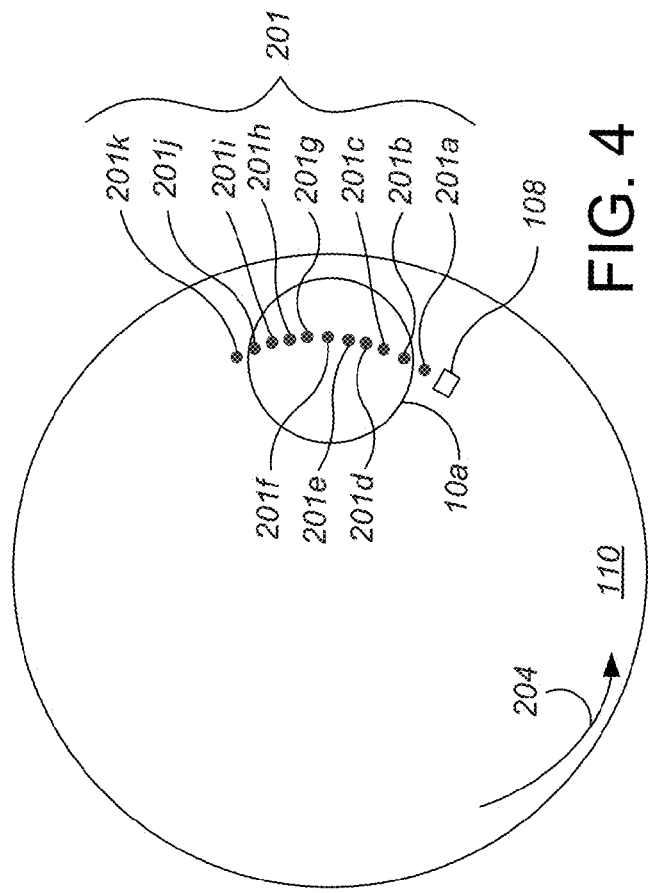
FIG. 4 illustrates a top view of a polishing pad and shows locations where in-situ measurements are taken on a substrate.

As shown by in FIG. 4, if the detector is installed in the platen, due to the rotation of the platen (shown by arrow 204), as the window 108 travels below a carrier head, the optical monitoring system making spectra measurements at a sampling frequency will cause the spectra measurements to be taken at locations 201 in an arc that traverses the substrate 10. For example, each of points 201a-201k represents a location of a spectrum measurement by the monitoring system (the number of points is illustrative; more or fewer measurements can be taken than illustrated, depending on the sampling frequency). The sampling frequency can be selected so that between five and twenty spectra are collected per sweep of the window 108. For example, the sampling period can be between 3 and 100 milliseconds.

As shown, over one rotation of the platen, spectra are obtained from different radii on the substrate 10. That is, some spectra are obtained from locations closer to the center of the substrate 10 and some are closer to the edge. Thus, for any given scan of the optical monitoring system across a substrate, based on timing, motor encoder information, and optical detection of the edge of the substrate and/or retaining ring, the controller 190 can calculate the radial position (relative to the center of the substrate being scanned) for each measured spectrum from the scan. The polishing system can also include a rotary position sensor, e.g., a flange attached to an edge of the platen that will pass through a stationary optical interrupter, to provide additional data for determination of which substrate and the position on the substrate of the measured spectrum. The controller can thus associate the various measured spectra with the controllable zones 148b-148e (see FIG. 2) on the substrates 10a and 10b. In some implementations, the time of measurement of the spectrum can be used as a substitute for the exact calculation of the radial position.

Over multiple rotations of the platen, for each zone, a sequence of spectra can be obtained over time. Without being limited to any particular theory, the spectrum of light reflected from the substrate 10 evolves as polishing progresses (e.g., over multiple rotations of the platen, not during a single sweep across the substrate) due to changes in the thickness of the outermost layer, thus yielding a sequence of time-varying spectra. Moreover, particular spectra are exhibited by particular thicknesses of the layer stack.

In some implementations, the controller, e.g., the computing device, can be programmed to compare a measured spectrum to multiple reference spectra and to determine which reference spectrum provides the best match. In particular, the controller can be programmed to compare each spectrum from a sequence of measured spectra from each zone to multiple reference spectra to generate a sequence of best matching reference spectra for each zone.

As used herein, a reference spectrum is a predefined spectrum generated prior to polishing of the substrate. A reference spectrum can have a pre-defined association, i.e., defined prior to the polishing operation, with a value representing a time in the polishing process at which the spectrum is expected to appear, assuming that the actual polishing rate follows an expected polishing rate. Alternatively or in addition, the reference spectrum can have a pre-defined association with a value of a substrate property, such as a thickness of the outermost layer.

A reference spectrum can be generated empirically, e.g., by measuring the spectra from a test substrate, e.g., a test substrate having a known initial layer thicknesses. For example, to generate a plurality of reference spectra, a set-up substrate is polished using the same polishing parameters that would be used during polishing of device wafers while a sequence of spectra are collected. For each spectrum, a value is recorded representing the time in the polishing process at which the spectrum was collected. For example, the value can be an elapsed time, or a number of platen rotations. The substrate can be overpolished, i.e., polished past a desired thickness, so that the spectrum of the light that reflected from the substrate when the target thickness is achieved can be obtained.

In order to associate each spectrum with a value of a substrate property, e.g., a thickness of the outermost layer, the initial spectra and property of a "set-up" substrate with the same pattern as the product substrate can be measured pre-polish at a metrology station. The final spectrum and property can also be measured post-polish with the same metrology station or a different metrology station. The properties for spectra between the initial spectra and final spectra can be determined by interpolation, e.g., linear interpolation based on elapsed time at which the spectra of the test substrate was measured.

In addition to being determined empirically, some or all of the reference spectra can be calculated from theory, e.g., using an optical model of the substrate layers. For example, and optical model can be used to calculate a reference spectrum for a given outer layer thickness D. A value representing the time in the polishing process at which the reference spectrum would be collected can be calculated, e.g., by assuming that the outer layer is removed at a uniform polishing rate. For example, the time Ts for a particular reference spectrum can be calculated simply by assuming a starting thickness D0 and uniform polishing rate R (Ts=(D0−D)/R). As another example, linear interpolation between measurement times T1, T2 for the pre-polish and post-polish thicknesses D1, D2 (or other thicknesses measured at the metrology station) based on the thickness D used for the optical model can be performed (Ts=T2−T1*(D1−D)/(D1−D2)).

In some implementations, software can be used to automatically calculate multiple reference spectra. Since there are variations in the thicknesses of the underlying layers of the incoming substrates, the manufacturer can input a thickness range and a thickness increment for at least one of the underlying layers, e.g., for multiple underlying layers. The software will calculate a reference spectra for each combination of thicknesses of the underlying layers. Multiple reference spectra can be calculated for each thickness of the overlying layer.

For example, for polishing of the structure shown in FIG. 1B, the optical stack might include, in order, a layer of metal at the bottom, e.g., the conductive layer 14, the passivation layer, a lower low-k dielectric layer, an etch stop layer, an upper low-k dielectric layer, a TEOS layer, a barrier layer, and a layer of water (to represent the polishing liquid through which the light will be arriving). In one example, for the purpose of calculating the reference spectra, the barrier layer might range from 300 Å to 350 Å in 10 Å increments, the TEOS layer might range from 4800 Å to 5200 Å in 50 Å increments, and the upper low-k dielectric top layer might range from 1800 Å to 2200 Å in 20 Å increments. A reference spectrum is calculated for each combination of thicknesses of the layers. With these degrees of freedom, 9*6*21=1134 reference spectra would be calculated. However, other ranges and increments are possible for each layer.

To calculate the reference spectra, the following optical model can be used. The reflectance $R_{STACK}$ of the top layer p of a thin film stack can be calculated as $$R_{STACK} = \left| \frac{E_p^-}{E_p^+} \right|^2$$

where $E_p^+$ represents the electro-magnetic field strength of the incoming light beam and $E_p^-$ represents the electromagnetic field strength of the outgoing light beam.

The values $E_p^+$ and $E_p^-$ can be calculated as $$E_p^+ = (E_p + H_p/\mu_p)/2 \quad E_p^- = (E_p - H_p/\mu_p)/2$$

The fields E and H in an arbitrary layer j can be calculated using transfer-matrix methods from the fields E and H in an underlying layer. Thus, in a stack of layers 0, 1, ..., p−1, p (where layer 0 is the bottom layer and layer p is the outermost layer), for a given layer j>0, $E_j$ and $H_j$ can be calculated as $$\begin{bmatrix} E_j \\ H_j \end{bmatrix} = \begin{bmatrix} \cos g_j & \frac{i}{u_j}\sin g_j \\ i\mu_j \sin g_j & \cos g_j \end{bmatrix} \begin{bmatrix} E_{j-1} \\ H_{j-1} \end{bmatrix}$$

with $\mu_j=(n_j-ik_j)\cdot\cos\phi_j$ and $g_j=2\pi(n_j-ik_j)\cdot t_j\cdot\cos\phi_j/\lambda$, where $n_j$ is the index of refraction of layer j, $k_j$ is an extinction coefficient of layer j, $t_j$ is the thickness of layer j, $\phi_j$ is the incidence angle of the light to layer j, and $\lambda$ is the wavelength. For the bottom layer in the stack, i.e., layer j=0, $E_0=1$ and $H_0=\mu_0=(n_0-ik_0)\cdot\cos(\phi_0)$. The index of refraction n and the extinction coefficient k for each layer can be determined from scientific literature, and can be functions of wavelength. The incidence angle $\phi$ can be calculated from Snell's law.

The thickness t for a layer can be calculated from the thickness range and thickness increment input by the user for the layer, e.g., $t_j=T_{MINj}+k*T_{INCj}$ for k=0, 1, ..., for $t_j \leq T_{MAXj}$, where $T_{MINj}$ and $T_{MAXj}$ are the lower and upper boundaries of the range of thicknesses for layer j and $T_{INCj}$ is the thickness increment for layer j. The calculation can be iterated for each combination of thickness values of the layers.

A potential advantage of this technique is quick generation of a large number of reference spectra that can correspond to different combinations of thicknesses of layers on the substrate, thus improving likelihood of finding a good matching reference spectra and improving accuracy and reliability of the optical monitoring system.

As an example, the light intensity reflected from the substrate shown in FIG. 1C can be calculated as $$\begin{bmatrix} E_5 \\ H_5 \end{bmatrix} = \begin{bmatrix} \cos g_4 & \frac{i}{u_j}\sin g_4 \\ i\mu_4 \sin g_4 & \cos g_4 \end{bmatrix} \begin{bmatrix} \cos g_3 & \frac{i}{u_j}\sin g_3 \\ i\mu_3 \sin g_3 & \cos g_3 \end{bmatrix} \begin{bmatrix} \cos g_2 & \frac{i}{u_2}\sin g_2 \\ i\mu_2 \sin g_2 & \cos g_2 \end{bmatrix}$$
$$\begin{bmatrix} \cos g_1 & \frac{i}{u_1}\sin g_1 \\ i\mu_1 \sin g_1 & \cos g_1 \end{bmatrix} \begin{bmatrix} 1 \\ \mu_0 \end{bmatrix}$$

with values of $g_4$ and $\mu_4$ depending on the thickness, index of refraction and extinction coefficient of the outermost layer of the substrate 10, e.g., the upper dielectric layer 22, e.g., a low-k material, of $g_3$ and $\mu_3$ depending on the thickness, index of refraction and extinction coefficient of an underlying layer, e.g., the etch stop layer 20, e.g., SiCN, $g_2$ and $\mu_2$ depending on the thickness, index of refraction and extinction coefficient of another underlying layer, e.g., the lower dielectric layer 18, $g_1$ and $\mu_1$ depending on the thickness, index of refraction and extinction coefficient of another underlying layer, e.g., a passivation layer, e.g., SiN, and $\mu_0$ depending on the index of refraction and extinction coefficient of the bottom layer, e.g., the conductive layer 14, e.g., copper.

The reflectance $R_{STACK}$ can then be calculated as $$R_{STACK} = \frac{E_5 - \frac{H_5}{\mu_5}}{E_5 + \frac{H_5}{\mu_5}}$$

Although not shown, the presence of a layer of water over the substrate (to represent the polishing liquid through which the light will be arriving) can also be accounted for in the optical model.

The substrate and associated optical stack described above is only one possible assembly of layers, and many others are possible. For example, the optical stack described above uses a conductive layer at the bottom of the optical stack, which would be typical for a substrate in a back-end-of-line process. However, in a front-end-of-line process, or if the conductive layer is a transparent material, then the bottom of the optical stack can be the semiconductor wafer, e.g., silicon. As another example, some substrates may not include the lower dielectric layer.

In addition to variations of the layer thicknesses, the optical model can include variations in the spectral contribution of the metal layer. That is, depending on the pattern on the die being manufactured, some spectral measurements may be made in regions with high concentration of metal (e.g., from metal material 28 in the trenches), whereas other spectral measurements may be made in regions with lower concentration of metal.

The spectrum $R_{LIBRARY}$ that is added to the library ban be calculated as $$R_{LIBRARY} = \frac{R_{STACK}}{R_{BASELINE}}(1 - X) + X * R_{Metal}$$

where $R_{BASELINE}$ is the spectral reflectance of the material at the bottom of the optical stack, e.g., bare semiconductor, e.g., for a substrate in a front-end-of-line process, or bare metal, e.g., for a substrate in a back-end-of-line process. The bare semiconductor can be the reflectance off of bare silicon; the bare metal can be copper. X is the percentage contribution to the spectrum of the metal, e.g., copper, and $R_{Metal}$ is the reflectance spectrum from the metal, e.g., copper.

$R_{LIBRARY}$ can be a combination of multiple optical stack models. For example, there could be an $R_{STACK1}$ which is the spectral contribution of the topmost stack (comprising of CAP, dielectric, barrier, and copper substrate), and $R_{STACK2}$ which is the spectral contribution of the two topmost stacks (which is the dielectric and barrier from $R_{STACK1}$ plus the dielectric, barrier, and copper substrate that would reside beneath it). So the calculation for $R_{LIBRARY}$ could look something like:

$$R_{LIBRARY} = \frac{R_{STACK1}}{R_{BASELINE}} * (X) + \frac{R_{STACK2}}{R_{BASELINE}} * (Y) + (1 - X - Y) * R_{Metal}$$

where $X + Y < 1$.

In some implementations, e.g., if the metal layer 14 and the metal material 28 are the same material, e.g., copper, then $R_{BASELINE}$ and $R_{Metal}$ are the same spectrum, e.g., the spectrum for copper. The calculation of spectrum $R_{LIBRARY}$ can be iterated over multiple values for X. For example, X can vary between 0.0 and 1.0 at 0.2 intervals. Continuing the example of the stack shown in FIG. 1B, with these degrees of freedom, 9*6*21*6=6804 reference spectra would be calculated. A potential advantage of this technique is generation of reference spectra that can correspond to different concentrations of metal in the measured spot on the substrate, thus improving likelihood of finding a good matching reference spectra and improving accuracy and reliability of the optical monitoring system.

For some types of substrates, e.g., some layer structures and die patterns, the techniques described above for generation of a library of reference spectra based on an optical model can be sufficient. However, for some types of substrates, the reference spectra based on this optical model do not correspond to empirically measured spectra. Without being limited to any particular theory, as additional layers are added to the stack on the substrate, scattering of light increases, e.g., from the different patterned metal layers on the substrate. In short, as the number of metal layers increases, it becomes less likely that light from lower layers on the substrate will be reflected back to enter the optical fiber and reach the detector.

In some implementations, to simulate the scattering caused by increasing numbers of metal layers, a modified extinction coefficient can be used in the optical model for calculation of the reference spectra. The modified extinction coefficient is larger than the natural extinction coefficient for the material of the layer. An amount added to the extinction coefficient can be larger for layers closer to the wafer.

For example, in the equations above, the terms $\mu_j$ and $g_j$ can be replaced by $\mu'_j$ and $g'_j$, respectively, with $\mu'_j$ and $g'_j$ calculated as $$\mu'_j = (n_j - i(k_j + m_j)) \cdot \cos \phi_j \quad g'_j = 2\pi(n_j - i(k_j + m_j)) \cdot t_j \cdot \cos \phi_j / \lambda$$

where $m_j$ is an amount to increase the extinction coefficient of layer j. In general, $m_j$ is equal to or greater than 0, and can be up to 1. For layers near the top of the stack, $m_j$ can be small, e.g., 0. For deeper layers, $m_j$ can larger, e.g., 0.2, 0.4 or 0.6. The amount $m_j$ can increase monotonically as j decreases. The amount $m_j$ can be functions of wavelength, e.g., for a particular layer, $m_j$ can be greater at longer wavelengths or can be greater at shorter wavelengths.

Referring to FIGS. 5 and 6, a measured spectrum 300 (see FIG. 5) can be compared to reference spectra 320 from one or more libraries 310 (see FIG. 6). As used herein, a library of reference spectra is a collection of reference spectra which represent substrates that share a property in common. However, the property shared in common in a single library may vary across multiple libraries of reference spectra. For example, two different libraries can include reference spectra that represent substrates with two different underlying thicknesses. For a given library of reference spectra, variations in the upper layer thickness, rather than other factors (such as differences in wafer pattern, underlying layer thickness, or layer composition), can be primarily responsible for the differences in the spectral intensities.

Reference spectra 320 for different libraries 310 can be generated by polishing multiple "set-up" substrates with different substrate properties (e.g., underlying layer thicknesses, or layer composition) and collecting spectra as discussed above; the spectra from one set-up substrate can provide a first library and the spectra from another substrate with a different underlying layer thickness can provide a second library. Alternatively or in addition, reference spectra for different libraries can be calculated from theory, e.g., spectra for a first library can be calculated using the optical model with the underlying layer having a first thickness, and spectra for a second library can be calculated using the optical model with the underlying layer having a different one thickness. For example, this disclosure uses a copper substrate for generating the library and later for spectra measurements.

In some implementations, each reference spectrum 320 is assigned an index value 330. In general, each library 310 can include many reference spectra 320, e.g., one or more, e.g., exactly one, reference spectra for each platen rotation over the expected polishing time of the substrate. This index 330 can be the value, e.g., a number, representing the time in the polishing process at which the reference spectrum 320 is expected to be observed. The spectra can be indexed so that each spectrum in a particular library has a unique index value. The indexing can be implemented so that the index values are sequenced in an order in which the spectra of a test substrate were measured. An index value can be selected to change monotonically, e.g., increase or decrease, as polishing progresses. In particular, the index values of the reference spectra can be selected so that they form a linear function of time or number of platen rotations (assuming that the polishing rate follows that of the model or test substrate used to generate the reference spectra in the library). For example, the index value can be proportional, e.g., equal, to a number of platen rotations at which the reference spectra was measured for the test substrate or would appear in the optical model. Thus, each index value can be a whole number. The index number can represent the expected platen rotation at which the associated spectrum would appear.

The reference spectra and their associated index values can be stored in a reference library. For example, each reference spectrum 320 and its associated index value 330 can be stored in a record 340 of database 350. The database 350 of reference libraries of reference spectra can be implemented in memory of the computing device of the polishing apparatus.

As noted above, for each zone of each substrate, based on the sequence of measured spectra or that zone and substrate, the controller 190 can be programmed to generate a sequence of best matching spectra. A best matching reference spectrum can be determined by comparing a measured spectrum to the reference spectra from a particular library.

In some implementations, the best matching reference spectrum can be determined by calculating, for each reference spectrum, a sum of squared differences between the measured spectrum and the reference spectrum. The reference spectrum with the lowest sum of squared differences has the best fit. Other techniques for finding a best matching reference spectrum are possible, e.g., lowest sum of absolute differences.

In some implementations, the best matching reference spectrum can be determined by using a matching technique other than sum of squared differences. In one implementation, for each reference spectrum, a cross-correlation between the measured spectrum and the reference spectrum is calculated, and the reference spectrum with the greatest correlation is selected as the matching reference spectrum. A potential advantage of cross-correlation is that it is less sensitive to lateral shift of a spectrum, and thus can be less sensitive to underlying thickness variation. In order to perform the cross-correlation, the leading and trailing ends of the measured spectrum can be padded with "zeros" to provide data to compare against the reference spectrum as the reference spectrum is shifted relative to the measured spectrum. Alternatively, the leading end of the measured spectrum can be padded with values equal to the value at the leading edge of the measured spectrum, and the trailing end of the measured spectrum can be padded with values equal to the value at the trailing edge of the measured spectrum. Fast Fourier transforms can be used to increase the speed of calculation of the cross-correlation for real-time application of the matching technique.

In another implementation, a sum of enclidean vector distances, e.g., $D=1/(\lambda a-\lambda b)\cdot[\Sigma_{\lambda=\lambda a\ to\ \lambda b}|I_M(\lambda)^2-I_R(\lambda)^2|]$, where $\lambda a$ to $\lambda b$ is wavelength summed over, calculated, $I_M(\lambda)$ is the measured spectrum, and $I_R(\lambda)$ is the reference spectrum. In another implementation, for each reference spectrum, a sum of derivative differences, e.g., $D=1/(\lambda a-\lambda b)\cdot[\Sigma_{\lambda=\lambda a\ to\ \lambda b}|dI_M(\lambda)/d\lambda-dI_R(\lambda)/d\lambda|]$, and the reference spectrum with the lowest sum is selected as the matching reference spectrum.

Figure 17:
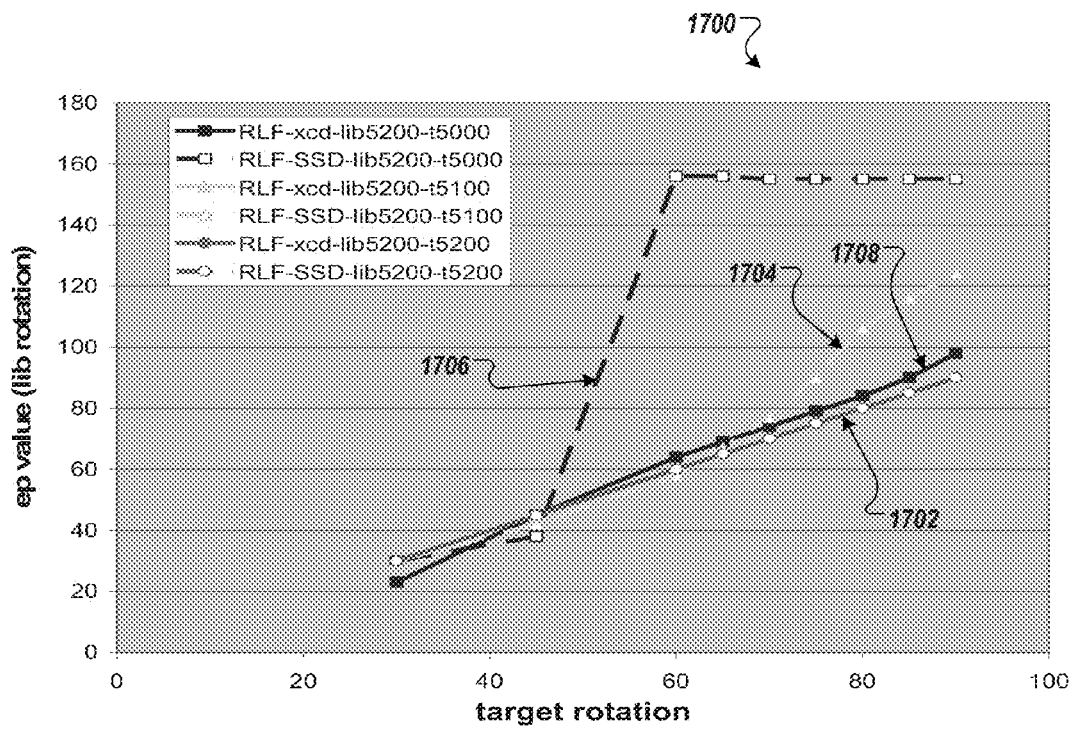
FIG. 17 is a graph showing a comparison of different techniques for determining a best matching reference spectrum.

FIG. 17 illustrates a comparison of index traces (indexes of best matching reference spectra as a function number of platen rotations) for spectra matching using cross-correlation and sum of squared differences methods for substrates with different thicknesses of the TEOS layer. The data was generated for product substrates having a stack of 1500 Å thick layer of Black Diamond, a 130 Å thick layer of Blok, and a TEOS layer that is 5200 Å, 5100 Å or 5000 Å thick. A reference library was generated for a reference substrate having a TEOS layer that is 5200 Å thick. As shown by trace 1702, where the product substrate and the reference substrate have a TEOS layer of the same thickness, i.e., 5200 Å, the two index traces overlap with no appreciable difference. However, where product substrate has a TEOS layer that is 5100 Å thick and the reference substrate has a TEOS layer 5200 Å thick, the index trace 1704 generated using sum of squared differences has some departure from linear behavior. In contrast, the index trace generated using cross-correlation overlaps the index trace 1702 (and is thus not visible in the graph). Finally, where product substrate has a TEOS layer that is 5000 Å thick and the reference substrate has a TEOS layer 5200 Å thick, the index trace 1706 generated using sum of squared differences has a significant departure from linear behavior and the trace 1702, whereas the index trace 1708 generated using cross-correlation remains generally linear and much closer to the trace 1702. In sum, this shows that using cross-correlation to determine the best matching spectrum results in a trace that better matches the ideal when there are variations in the thickness of the underlying layer.

In some implementations, the measured raw spectra are normalized as part of the process of determining the best matching reference spectrum. The normalized spectrum is then compared, e.g., by calculating the sum of squared differences, cross-correlation, or the like, to the reference spectra to determine the best match.

For example, a base layer reference spectrum can be stored, and normalizing can include a division operation in which the raw spectrum is in the numerator and the base layer reference spectrum is in the denominator. The base layer reference spectrum can be a spectrum of the material of the bottommost layer that light would be expected to reach. For example, the base layer reference spectrum can be a metal reference spectrum, e.g., for a back-end-of-line process (since in a back-end-of-line process the bottommost layer that light would be expected to reach would be a metal layer). For example, if the material of the bottommost layer is copper, then the metal reference spectrum can be a spectrum of a copper layer. As another example, the base layer reference spectrum can be a silicon reference spectrum, e.g., for a front-end-of-line process (since in a front-end-of-line process the bottommost layer that light would be expected to reach would be the silicon wafer). To obtain the base layer reference spectrum, the spectrum of a blank wafer (no pattern) having only the exposed material can be measured by the in-situ optical monitoring system. For example, the metal reference spectrum can be obtained by measuring the spectrum of light reflecting of a copper disk or off a thick copper layer deposited on a silicon wafer.

A measured spectrum can be normalized as follows:

$$R=(A-D_A)/(B-D_B)$$

where R is the normalized spectrum, A is the raw spectrum, $D_A$ and $D_B$ are dark spectrums obtained under the dark condition, and B is the base layer reference spectrum. A dark spectrum is a spectrum measured by the in-situ optical monitoring system when no substrate is being measured by the in-situ optical monitoring system. In some implementations, $D_A$ and $D_B$ are the same spectrum. For example, $D_A$ and $D_B$ could be a dark spectrum collected when the base layer reference spectrum is collected, e.g., at the same platen rotation. In some implementations, $D_A$ is a dark spectrum collected when the raw spectrum is collected, e.g., at the same platen rotation, and $D_B$ is a dark spectrum collected when the base layer reference spectrum is collected, e.g., at the same platen rotation.

Normalizing the measured spectra can remove light reflections contributed by mediums other than the film or films of interest, and can facilitates their comparison to the reference spectra. Light reflections contributed by media other than the film or films of interest include light reflections from the polishing pad window and from the base metal or silicon layer of the substrate.

Although fairly complex layer stacks are described, this normalization approach would still be applicable for a much simpler substrate, e.g., just a single layer or two layers over a metal layer, just a single layer or two layers over a silicon wafer, as well as layer stacks of intermediate and greater complexity.

Figure 7:
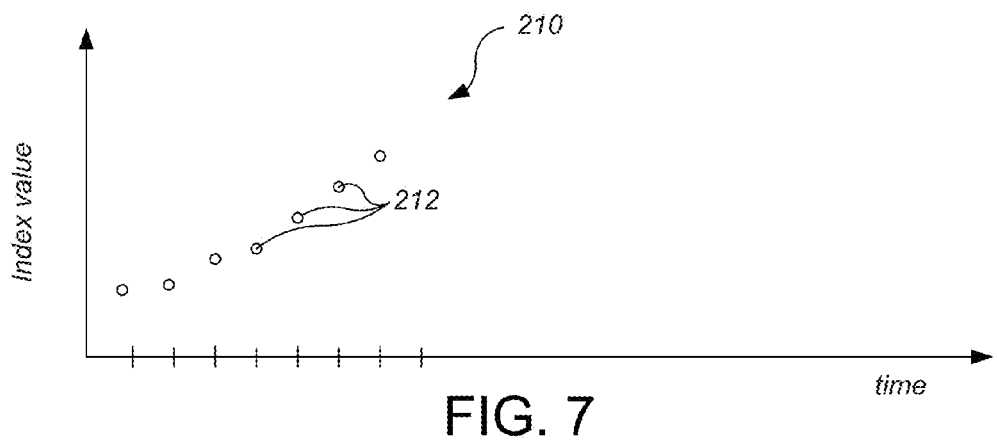
FIG. 7 illustrates an index trace.

Now referring to FIG. 7, which illustrates the results for only a single zone of a single substrate, the index value of each of the best matching spectra in the sequence can be determined to generate a time-varying sequence of index values 212. This sequence of index values can be termed an index trace 210. In some implementations, an index trace is generated by comparing each measured spectrum to the reference spectra from exactly one library. In general, the index trace 210 can include one, e.g., exactly one, index value per sweep of the optical monitoring system below the substrate.

For a given index trace 210, where there are multiple spectra measured for a particular zone in a single sweep of the optical monitoring system (termed "current spectra"), a best match can be determined between each of the current spectra and the reference spectra of one or more, e.g., exactly one, library. In some implementations, each selected current spectra is compared against each reference spectra of the selected library or libraries. Given current spectra e, f, and g, and reference spectra E, F, and G, for example, a matching coefficient could be calculated for each of the following combinations of current and reference spectra: e and E, e and F, e and G, f and E, f and F, f and G, g and E, g and F, and g and G. Whichever matching coefficient indicates the best match, e.g., is the smallest, determines the best-matching reference spectrum, and thus the index value. Alternatively, in some implementations, the current spectra can be combined, e.g., averaged, and the resulting combined spectrum is compared against the reference spectra to determine the best match, and thus the index value.

A method that can be applied to decrease computer processing is to limit the portion of the library that is searched for matching spectra. The library typically includes a wider range of spectra than will be obtained while polishing a substrate. During substrate polishing, the library searching is limited to a predetermined range of library spectra. In some embodiments, the current rotational index N of a substrate being polished is determined. For example, in an initial platen rotation, N can be determined by searching all of the reference spectra of the library. For the spectra obtained during a subsequent rotation, the library is searched within a range of freedom of N. That is, if during one rotation the index number is found to be N, during a subsequent rotation which is X rotations later, where the freedom is Y, the range that will be searched from (N+X)−Y to (N+X)+Y.

In some implementations, for at least some zones of some substrates, a plurality of index traces can be generated. For a given zone of a given substrate, an index trace can be generated for each reference library of interest. That is, for each reference library of interest to the given zone of the given substrate, each measured spectrum in a sequence of measured spectra is compared to reference spectra from a given library, a sequence of the best matching reference spectra is determined, and the index values of the sequence of best matching reference spectra provide the index trace for the given library.

In summary, each index trace includes a sequence 210 of index values 212, with each particular index value 212 of the sequence being generated by selecting the index of the reference spectrum from a given library that is the closest fit to the measured spectrum. The time value for each index of the index trace 210 can be the same as the time at which the measured spectrum was measured.

An in-situ monitoring technique is used to detect clearing of the second layer and exposure of the underlying layer or layer structure. For example, exposure of the first layer at a time TC can be detected by a sudden change in the motor torque or total intensity of light reflected from the substrate, or from dispersion of the collected spectra as discussed in greater detail below.

Figure 8:
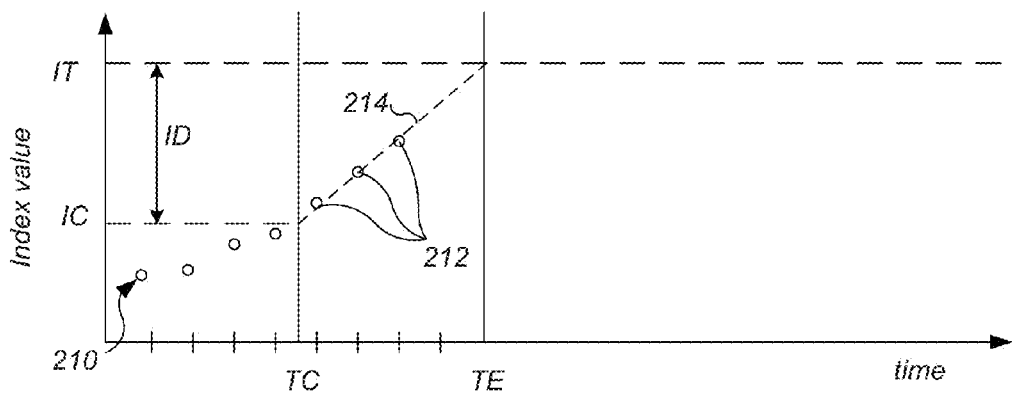
FIG. 8 illustrates an index trace having a linear function fit to index values collected after clearance of an overlying layer is detected.

As shown in FIG. 8, a function, e.g., a polynomial function of known order, e.g., a first-order function (e.g., a line 214) is fit to the sequence of index values of spectra collected after time TC, e.g., using robust line fitting. Index values for spectra collected before the time TC are ignored when fitting the function to the sequence of index values. Other functions can be used, e.g., polynomial functions of second-order, but a line provides ease of computation. Polishing can be halted at an endpoint time TE that the line 214 crosses a target index IT.

Figure 9:
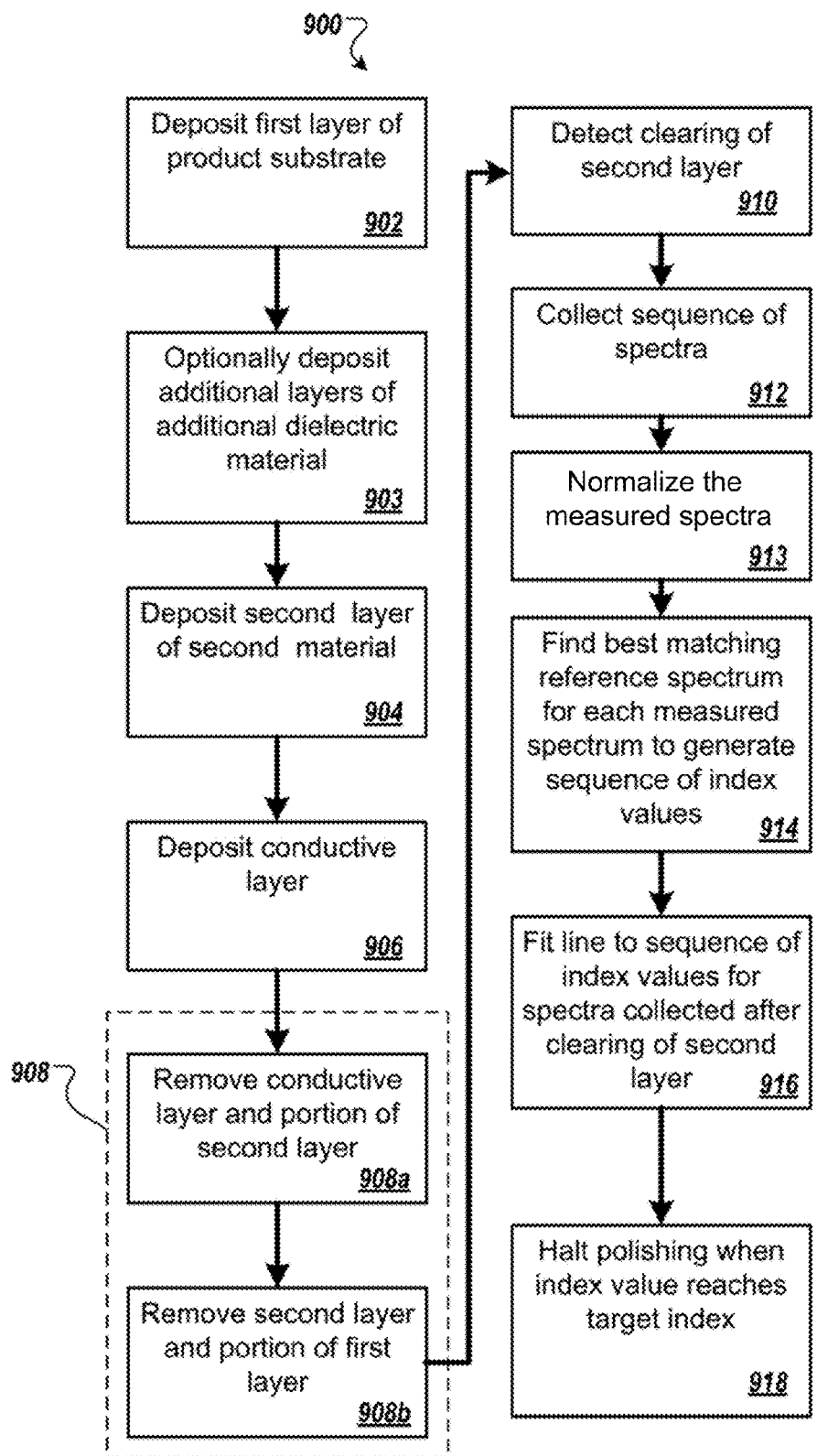
FIG. 9 is a flow diagram of an example process for fabricating a substrate and detecting a polishing endpoint.

FIG. 9 shows a flow chart of a method of fabricating and polishing a product substrate. The product substrate can have at least the same layer structure and the same pattern, as the test substrates used to generate the reference spectra of the library.

Initially, the first layer is deposited on the substrate and patterned (step 902). As noted above, the first layer can be a dielectric, e.g., a low-k material, e.g., carbon doped silicon dioxide, e.g., Black Diamond™ (from Applied Materials, Inc.) or Coral™ (from Novellus Systems, Inc.). Alternatively, the a first layer can include polysilicon, e.g., consist of substantially pure polysilicon, or be a combination of polysilicon and dielectric material.

Optionally, depending on the composition of the first material, one or more additional layers of another dielectric material, different from both the first material, e.g., a low-k capping material, e.g., tetraethyl orthosilicate (TEOS), is deposited over the first layer on the product substrate (step 903). Together, the first layer and the one or more additional layers provide a layer stack. Optionally, patterning can occur after depositing of the one or more additional layers (so that the one or more additional layers do not extend into the trench in the first layer, as shown in FIG. 1A).

Next, the second layer of a different material, e.g., a barrier layer, e.g., a nitride, e.g., tantalum nitride or titanium nitride, is deposited over the first layer or layer stack of the product substrate (step 904). In addition, a conductive layer, e.g., a metal layer, e.g., copper, can be deposited over the second layer of the product substrate (and in trenches provided by the pattern of the first layer) (step 906). Optionally, patterning of the first layer can occur after depositing of the second layer (in which case the second layer would not extend into the trench in the first layer).

The product substrate is polished (step 908). For example, the conductive layer and a portion of the second layer can be polished and removed at a first polishing station using a first polishing pad (step 908a). Then the second layer and a portion of the first layer can be polished and removed at a second polishing station using a second polishing pad (step 908b). However, it should be noted that for some implementations, there is no conductive layer, e.g., the second layer is the outermost layer when polishing begins. Of course, steps 902-906 can be performed elsewhere, so that the process for a particular operator of the polishing apparatus begins with step 908.

An in-situ monitoring technique is used to detect clearing of the second layer and exposure of the first layer (step 910). For example, exposure of the first layer at a time TC (see FIG. 8) can be detected by a sudden change in the motor torque or total intensity of light reflected from the substrate, or from dispersion of the collected spectra as discussed in greater detail below.

In some implementations, there is no overlying layer to be removed, i.e., polishing begins with the first layer, in which case steps 903-910 can be omitted, and steps that begin with the clearance of the second layer can instead begin immediately upon or with a few second delay after commencing polishing of the first layer.

Beginning at least with detection of the clearance of second layer (and potentially earlier, e.g., from the beginning of polishing of the product substrate with the second polishing pad), a sequence of measured spectra are obtained during polishing (step 912), e.g., using the in-situ monitoring system described above.

The measured spectra are analyzed to generate a sequence of index values, and a function is fit to the sequence of index values. In particular, for each measured spectrum in the sequence of measured spectra, the index value for the reference spectrum that is the best fit is determined to generate the sequence of index values (step 914). Optionally, the measured spectra can be normalized, as discussed above, e.g., as part of the process of determining the best matching fitting reference spectrum (step 913). A function, e.g., a linear function, is fit to the sequence of index values for the spectra collected after the time TC at which clearance of the second layer is detected (step 916). Index values for spectra collected before the time TC at which clearance of the second layer is detected need not be used in the calculation of the function.

Polishing can be halted once the index value (e.g., a calculated index value generated from the linear function fit to the new sequence of index values) reaches target index (step 918). The target thickness IT can be set by the user prior to the polishing operation and stored. Alternatively, a target amount to remove can be set by the user, and a target index IT can be calculated from the target amount to remove. For example, an index difference ID can be calculated from the target amount to remove, e.g., from an empirically determined ratio of amount removed to the index (e.g., the polishing rate), and adding the index difference ID to the index value IC at the time TC that clearance of the overlying layer is detected (see FIG. 8).

It is also possible to use the function fit to the index values from spectra collected after clearance of the second layer is detected to adjust the polishing parameters, e.g., to adjust the polishing rate of one or more zones on a substrate to improve polishing uniformity.

Figure 10:
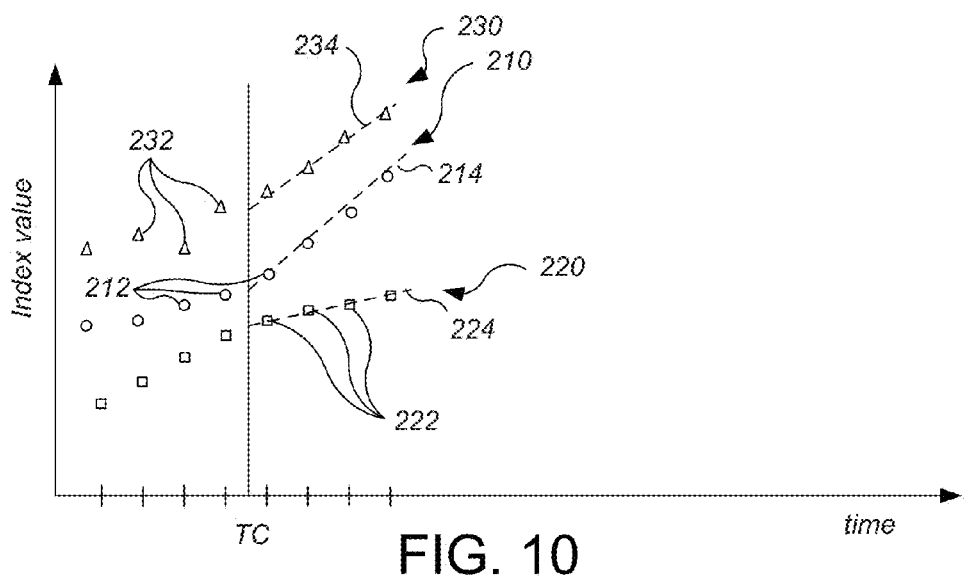
FIG. 10 illustrates a plurality of index traces.

Referring to FIG. 10, a plurality of index traces is illustrated. As discussed above, an index trace can be generated for each zone. For example, a first sequence 210 of index values 212 (shown by hollow circles) can be generated for a first zone, a second sequence 220 of index values 222 (shown by hollow squares) can be generated for a second zone, and a third sequence 230 of index values 232 (shown by hollow triangles) can be generated for a third zone. Although three zones are shown, there could be two zones or four or more zones. All of the zones can be on the same substrate, or some of the zones can be from different substrates being polished simultaneously on the same platen.

As discussed above, an in-situ monitoring technique is used to detect clearing of the second layer and exposure of the underlying layer or layer structure. For example, exposure of the first layer at a time TC can be detected by a sudden change in the motor torque or total intensity of light reflected from the substrate, or from dispersion of the collected spectra as discussed in greater detail below.

For each substrate index trace, a polynomial function of known order, e.g., a first-order function (e.g., a line) is fit to the sequence of index values of spectra collected after time TC for the associated zone, e.g., using robust line fitting. For example, a first line 214 can be fit to index values 212 for the first zone, a second line 224 can be fit to the index values 222 of the second zone, and a third line 234 can be fit to the index values 232 of the third zone. Fitting of a line to the index values can include calculation of the slope S of the line and an x-axis intersection time T at which the line crosses a starting index value, e.g., 0. The function can be expressed in the form $I(t)=S \cdot (t-T)$, where t is time. The x-axis intersection time T can have a negative value, indicating that the starting thickness of the substrate layer is less than expected. Thus, the first line 214 can have a first slope S1 and a first x-axis intersection time T1, the second line 224 can have a second slope S2 and a second x-axis intersection time T2, and the third line 234 can have a third slope S3 and a third x-axis intersection time T3.

At some time during the polishing process, e.g., at a time T0, a polishing parameter for at least one zone is adjusted to adjust the polishing rate of the zone of the substrate such that at a polishing endpoint time, the plurality of zones are closer to their target thickness than without such adjustment. In some embodiments, each zone can have approximately the same thickness at the endpoint time.

Figure 11:
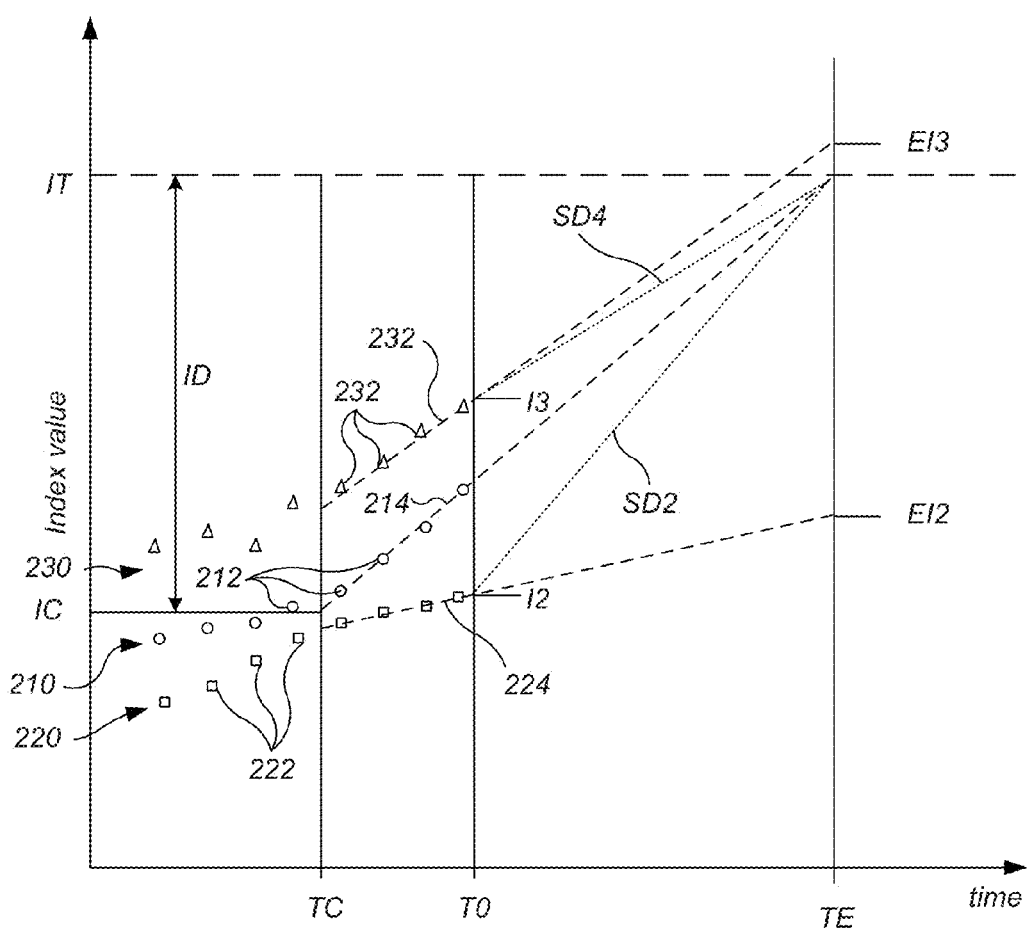
FIG. 11 illustrates a calculation of a plurality of desired slopes for a plurality of adjustable zones based on a time that an index trace of a reference zone reaches a target index.

Referring to FIG. 11, in some implementations, one zone is selected as a reference zone, and a projected endpoint time TE at which the reference zone will reach a target index IT is determined. For example, as shown in FIG. 11, the first zone is selected as the reference zone, although a different zone and/or a different substrate could be selected. The target thickness IT is set by the user prior to the polishing operation and stored. Alternatively, a target amount to remove TR can be set by the user, and a target index IT can be calculated from the target amount to remove TR. For example, an index difference ID can be calculated from the target amount to remove, e.g., from an empirically determined ratio of amount removed to the index (e.g., the polishing rate), and adding the index difference ID to the index value IC at the time TC that clearance of the overlying layer is detected.

In order to determine the projected time at which the reference zone will reach the target index, the intersection of the line of the reference zone, e.g., line 214, with the target index, IT, can be calculated. Assuming that the polishing rate does not deviate from the expected polishing rate through the remainder polishing process, then the sequence of index values should retain a substantially linear progression. Thus, the expected endpoint time TE can be calculated as a simple linear interpolation of the line to the target index IT, e.g., IT=S·(TE−T). Thus, in the example of FIG. 11 in which the first zone is selected as the reference zone, with associated first line 214, IT=S1·(TE−T1), i.e., TE=IT/S1−T1.

One or more zones, e.g., all zones, other than the reference zone (including zones on other substrates) can be defined as adjustable zones. Where the lines for the adjustable zones meet the expected endpoint time TE define projected endpoint for the adjustable zones. The linear function of each adjustable zone, e.g., lines 224 and 234 in FIG. 11, can thus be used to extrapolate the index, e.g., EI2 and EI3, that will be achieved at the expected endpoint time ET for the associated zone. For example, the second line 224 can be used to extrapolate the expected index, EI2, at the expected endpoint time ET for the second zone, and the third line 234 can be used to extrapolate the expected index, EI3, at the expected endpoint time ET for the third zone.

As shown in FIG. 11, if no adjustments are made to the polishing rate of any of the zones after time T0, then if endpoint is forced at the same time for all zones, then each zone can have a different thickness (which is not desirable because it can lead to defects and loss of throughput).

If the target index will be reached at different times for different zones (or equivalently, the adjustable zones will have different expected indexes at the projected endpoint time of the reference zone), the polishing rate can be adjusted upwardly or downwardly, such that the zones would reach the target index (and thus target thickness) closer to the same time than without such adjustment, e.g., at approximately the same time, or would have closer to the same index value (and thus same thickness), at the target time than without such adjustment, e.g., approximately the same index value (and thus approximately the same thickness).

Thus, in the example of FIG. 11, commencing at a time T0, at least one polishing parameter for the second zone is modified so that the polishing rate of the zone is increased (and as a result the slope of the index trace 220 is increased). Also, in this example, at least one polishing parameter for the third zone is modified so that the polishing rate of the third zone is decreased (and as a result the slope of the index trace 230 is decreased). As a result the zones would reach the target index (and thus the target thickness) at approximately the same time (or if pressure to the zones halts at the same time, the zones will end with approximately the same thickness).

In some implementations, if the projected index at the expected endpoint time ET indicate that a zone of the substrate is within a predefined range of the target thickness, then no adjustment may be required for that zone. The range may be 2%, e.g., within 1%, of the target index.

The polishing rates for the adjustable zones can be adjusted so that all of the zones are closer to the target index at the expected endpoint time than without such adjustment. For example, a reference zone of the reference substrate might be chosen and the processing parameters for all of the other zone adjusted such that all of the zones will endpoint at approximately the projected time of the reference substrate. The reference zone can be, for example, a predetermined zone, e.g., the center zone 148a or the zone 148b immediately surrounding the center zone, the zone having the earliest or latest projected endpoint time of any of the zones of any of the substrates, or the zone of a substrate having the desired projected endpoint. The earliest time is equivalent to the thinnest substrate if polishing is halted at the same time. Likewise, the latest time is equivalent to the thickest substrate if polishing is halted at the same time. The reference substrate can be, for example, a predetermined substrate, a substrate having the zone with the earliest or latest projected endpoint time of the substrates. The earliest time is equivalent to the thinnest zone if polishing is halted at the same time. Likewise, the latest time is equivalent to the thickest zone if polishing is halted at the same time.

For each of the adjustable zones, a desired slope for the index trace can be calculated such that the adjustable zone reaches the target index at the same time as the reference zone. For example, the desired slope SD can be calculated from (IT−I)=SD*(TE−T0), where I is the index value (calculated from the linear function fit to the sequence of index values) at time T0 polishing parameter is to be changed, IT is the target index, and TE is the calculated expected endpoint time. In the example of FIG. 11, for the second zone the desired slope SD2 can be calculated from (IT−I2)=SD2*(TE−T0), and for the third zone the desired slope SD3 can be calculated from (IT−I3)=SD3*(TE−T0).

Alternatively, in some implementations, there is no reference zone, and the expected endpoint time can be a predetermined time, e.g., set by the user prior to the polishing process, or can be calculated from an average or other combination of the expected endpoint times of two or more zones (as calculated by projecting the lines for various zones to the target index) from one or more substrates. In this implementation, the desired slopes are calculated substantially as discussed above, although the desired slope for the first zone of the first substrate must also be calculated, e.g., the desired slope SD1 can be calculated from (IT−I1)=SD1*(TE'−T0).

Alternatively, in some implementations, there are different target indexes for different zones. This permits the creation of a deliberate but controllable non-uniform thickness profile on the substrate. The target indexes can be entered by user, e.g., using an input device on the controller. For example, the first zone of the first substrate can have a first target index, the second zone of the first substrate can have a second target index, the first zone of the second substrate can have a third target index, and the second zone of the second substrate can have a fourth target index.

For any of the above methods described above, the polishing rate is adjusted to bring the slope of index trace closer to the desired slope. The polishing rates can be adjusted by, for example, increasing or decreasing the pressure in a corresponding chamber of a carrier head. The change in polishing rate can be assumed to be directly proportional to the change in pressure, e.g., a simple Prestonian model. For example, for each zone of each substrate, where zone was polished with a pressure Pold prior to the time T0, a new pressure Pnew to apply after time T0 can be calculated as Pnew=Pold*(SD/S), where S is the slope of the line prior to time T0 and SD is the desired slope.

For example, assuming that pressure Pold1 was applied to the first zone of the first substrate, pressure Pold2 was applied to the second zone of the first substrate, pressure Pold3 was applied to the first zone of the second substrate, and pressure Pold4 was applied to the second zone of the second substrate, then new pressure Pnew1 for the first zone of the first substrate can be calculated as Pnew1=Pold1* (SD1/S1), the new pressure Pnew2 for the second zone of the first substrate clan be calculated as Pnew2=Pold2*(SD2/S2), the new pressure Pnew3 for the first zone of the second substrate clan be calculated as Pnew3=Pold3*(SD3/S3), and the new pressure Pnew4 for the second zone of the second substrate clan be calculated as Pnew4=Pold4*(SD4/S4).

The process of determining projected times that the substrates will reach the target thickness, and adjusting the polishing rates, can be performed just once during the polishing process, e.g., at a specified time, e.g., 40 to 60% through the expected polishing time, or performed multiple times during the polishing process, e.g., every thirty to sixty seconds. At a subsequent time during the polishing process, the rates can again be adjusted, if appropriate. During the polishing process, changes in the polishing rates can be made only a few times, such as four, three, two or only one time. The adjustment can be made near the beginning, at the middle or toward the end of the polishing process.

Polishing continues after the polishing rates have been adjusted, e.g., after time T0, the optical monitoring system continues to collect spectra for at least the reference zone and determine index values for the reference zone. In some implementations, the optical monitoring system continues to collect spectra and determine index values for each zone. Once the index trace of a reference zone reaches the target index, endpoint is called and the polishing operation stops.

Figure 12:
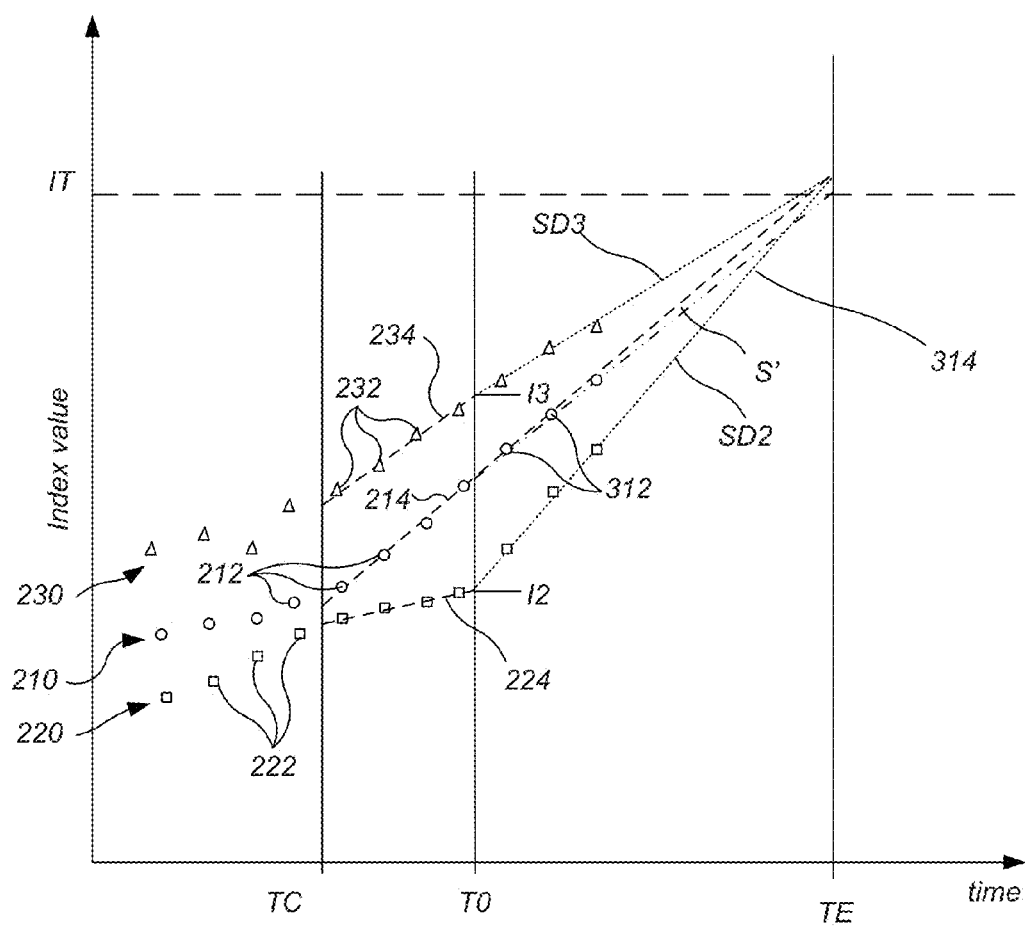
FIG. 12 illustrates a calculation of an endpoint for based on a time that an index trace of a reference zone reaches a target index.

For example, as shown in FIG. 12, after time T0, the optical monitoring system continues to collect spectra for the reference zone and determine index values 312 for the reference zone. If the pressure on the reference zone did not change (e.g., as in the implementation of FIG. 11), then the linear function can be calculated using data points from both before T0 (but not before TC) and after T0 to provide an updated linear function 314, and the time at which the linear function 314 reaches the target index IT indicates the polishing endpoint time. On the other hand, if the pressure on the reference zone changed at time T0, then a new linear function 314 with a slope S' can be calculated from the sequence of index values 312 after time T0, and the time at which the new linear function 314 reaches the target index IT indicates the polishing endpoint time. The reference zone used for determining endpoint can be the same reference zone used as described above to calculate the expected endpoint time, or a different zone (or if all of the zones were adjusted as described with reference to FIG. 11, then a reference zone can be selected for the purpose of endpoint determination). If the new linear function 314 reaches the target index IT slightly later (as shown in FIG. 12) or earlier than the projected time calculated from the original linear function 214, then one or more of the zones may be slightly overpolished or underpolished, respectively. However, since the difference between the expected endpoint time and the actual polishing time should be less than a couple seconds, this need not severely impact the polishing uniformity.

In some implementations, e.g., for copper polishing, after detection of the endpoint for a substrate, the substrate is immediately subjected to an overpolishing process, e.g., to remove copper residue. The overpolishing process can be at a uniform pressure for all zones of the substrate, e.g., 1 to 1.5 psi. The overpolishing process can have a preset duration, e.g., 10 to 15 seconds.

Where multiple index traces are generated for a particular zone, e.g., one index trace for each library of interest to the particular zone, then one of the index traces can be selected for use in the endpoint or pressure control algorithm for the particular zone. For example, the each index trace generated for the same zone, the controller 190 can fit a linear function to the index values of that index trace, and determine a goodness of fit of that linear function to the sequence of index values. The index trace generated having the line with the best goodness of fit its own index values can be selected as the index trace for the particular zone and substrate. For example, when determining how to adjust the polishing rates of the adjustable zones, e.g., at time T0, the linear function with the best goodness of fit can be used in the calculation. As another example, endpoint can be called when the calculated index (as calculated from the linear function fit to the sequence of index values) for the line with the best goodness of fit matches or exceeds the target index. Also, rather than calculating an index value from the linear function, the index values themselves could be compared to the target index to determine the endpoint.

Determining whether an index trace associated with a spectra library has the best goodness of fit to the linear function associated with the library can include determining whether the index trace of the associated spectra library has the least amount of difference from the associated robust line, relatively, as compared to the differences from the associated robust line and index trace associated with another library, e.g., the lowest standard deviation, the greatest correlation, or other measure of variance. In one implementation, the goodness of fit is determined by calculating a sum of squared differences between the index data points and the linear function; the library with the lowest sum of squared differences has the best fit.

Figure 13:
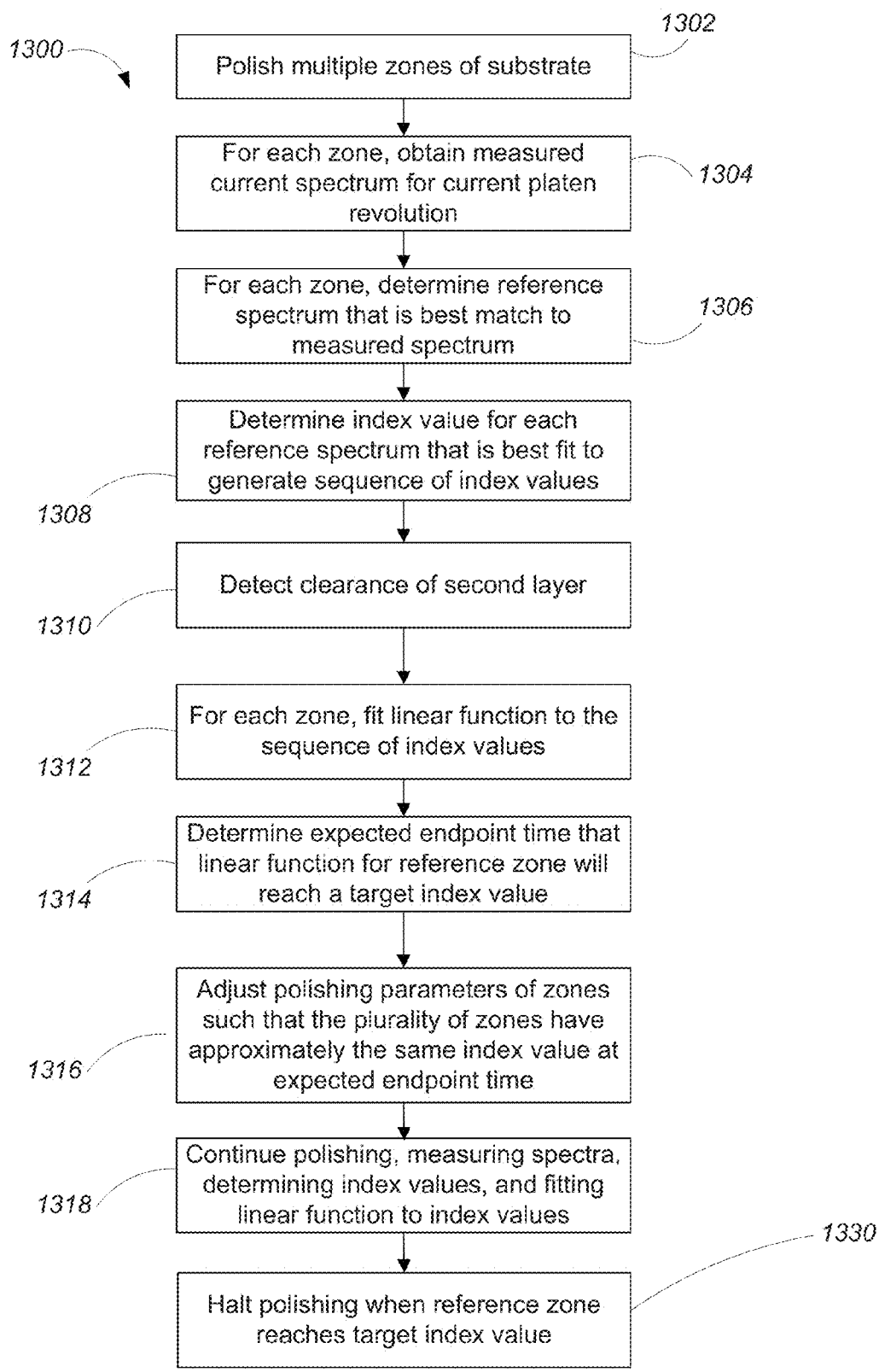
FIG. 13 is a flow diagram of an example process for adjusting the polishing rate of a plurality of zones in a plurality of substrates such that the plurality of zones have approximately the same thickness at the target time.

Referring to FIG. 13, a summary flow chart 1300 is illustrated. A plurality of zones of a substrate are polished in a polishing apparatus simultaneously with the same polishing pad (step 1302) as described above. During this polishing operation, each zone has its polishing rate controllable independently of the other substrates by an independently variable polishing parameter, e.g., the pressure applied by the chamber in carrier head above the particular zone. During the polishing operation, the substrate is monitored (step 1304) as described above, e.g., with a sequence of measure spectra obtained from each zone. For each measured spectrum in the sequence, the reference spectrum that is the best match is determined (step 1306). The index value for each reference spectrum that is the best fit is determined to generate sequence of index values (step 1308).

Clearance of the second layer is detected (step 1310). For each zone, a linear function is fit to the sequence of index values for spectra collected after clearance of the second layer is detected (step 1302). In one implementation, an expected endpoint time that the linear function for a reference zone will reach a target index value is determined, e.g., by linear interpolation of the linear function (step 1314). In other implementations, the expected endpoint time is predetermined or calculated as a combination of expected endpoint times of multiple zones. If needed, the polishing parameters for the other zones are adjusted to adjust the polishing rate of that substrate such that the plurality of zones reach the target thickness at approximately the same time or such that the plurality of zones have approximately the same thickness (or a target thickness) at the target time (step 1316). Polishing continues after the parameters are adjusted, and for each zone, measuring a spectrum, determining the best matching reference spectrum from a library, determining the index value for the best matching spectrum to generate a new sequence of index values for the time period after the polishing parameter has been adjusted, and fitting a linear function to index values (step 1318). Polishing can be halted once the index value for a reference zone (e.g., a calculated index value generated from the linear function fit to the new sequence of index values) reaches target index (step 1330).

In some implementations, the sequence of index values is used to adjust the polishing rate of one or more zones of a substrate, but another in-situ monitoring system or technique is used to detect the polishing endpoint.

As discussed above, for some techniques and some layer stacks, detection of clearance of the overlying layer and exposure of the underlying layer can be difficult. In some implementations, a sequence of groups of spectra are collected, and a value of a dispersion parameter is calculated for a each group of spectra to generate sequence of dispersion values. The clearance of the overlying layer can be detected from the sequence of dispersion values. This technique can be used to detect clearing of the second layer and exposure of the first layer, e.g., in steps 910 or 1310 of the polishing operations described above.

Figure 14:
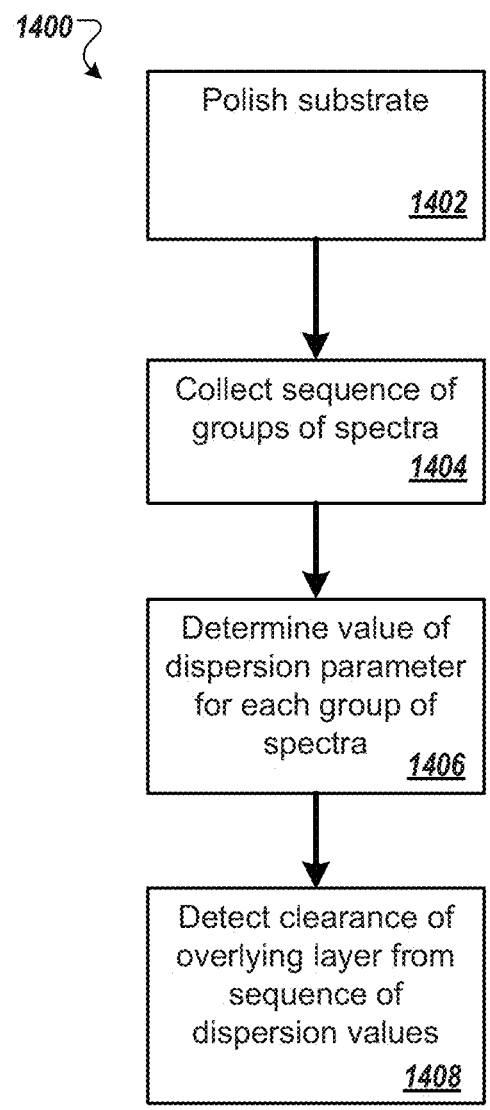
FIG. 14 shows a flow chart for detecting clearance of an overlying layer.

FIG. 14 shows a method 1400 for detecting clearance of the second layer and exposure of the first layer. As the substrate is being polished (step 1402), a sequence of groups of spectra are collected (step 1404). As shown in FIG. 4, if the optical monitoring system is secured to a rotating platen, then in a single sweep of the optical monitoring system across the substrate, spectra can be collected from multiple different locations 201b-201j on the substrate. The spectra collected from a single sweep provide a group of spectra. As polishing progresses, multiple sweeps of the optical monitoring system provide a sequence of groups of spectra. One group of spectra can be collected for each platen rotation, e.g., the groups can be collected at frequency equal to the platen rotation rate. Typically, each group will include five to twenty spectra. The spectra can be collected using the same optical monitoring system that is used to collect spectra for the peak tracking technique discussed above.

Figure 15A:
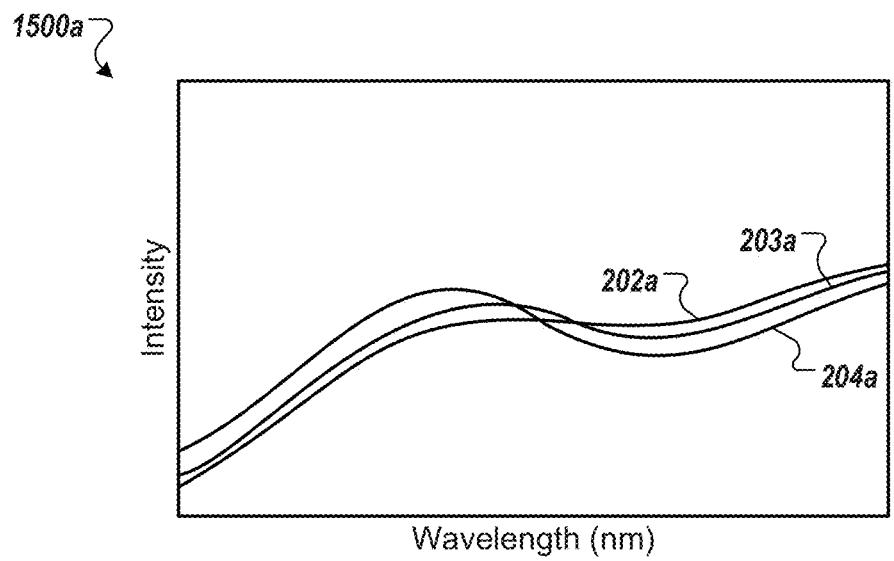
FIG. 15A shows a graph of spectra collected during a single sweep at the beginning of polishing.
Figure 15B:
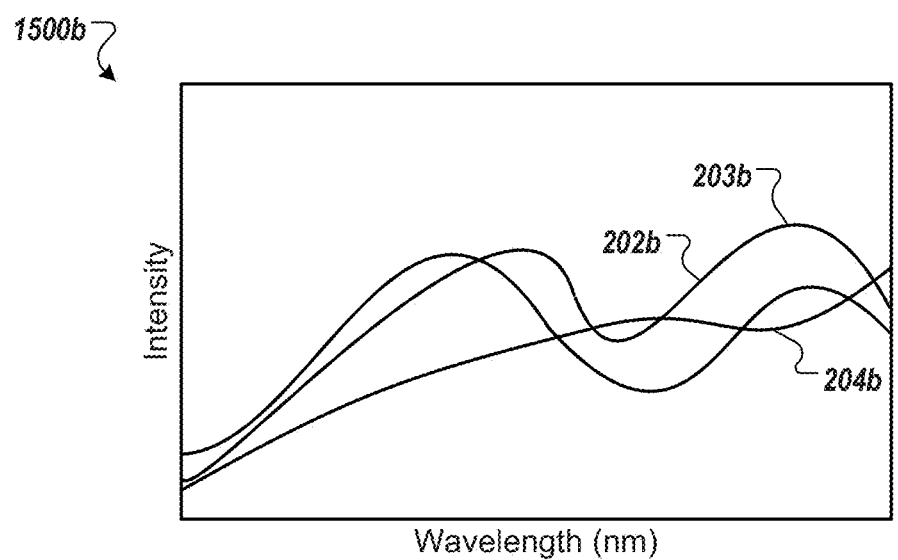
FIG. 15B shows a graph of spectra collected during a single sweep near barrier clearing.

FIG. 15A provides an example of a group of measured spectra 1500a of light reflected from the substrate 10 at the beginning of polishing, e.g., when a significant thickness of the overlying layer remains over the underlying layer. The group of spectra 1500a can include spectra 202a-204a collected at different locations on the substrate in a first sweep of the optical monitoring system across the substrate. FIG. 15B provides an example of a group of measured spectra 1500b of light reflected from the substrate 10 at or near clearance of the overlying layer. The group of spectra 1500b can include spectra 202b-204b collected at different locations on the substrate in a different second sweep of the optical monitoring system across the substrate (the spectra 1500a can be collected from different locations on the substrate than the spectra 1500b).

Initially, as shown in FIG. 15A, the spectra 1500a are fairly similar. However, as shown in FIG. 15B, as the overlying layer, e.g., a barrier layer, is cleared, and the underlying layer, e.g., a low-k or capping layer, is exposed, differences between the spectra 1500b from different locations on the substrate tend to become more pronounced.

For each group of spectra, a value of a dispersion parameter of the spectra in the group is calculated (step 1406). This generates a sequence of dispersion values.

In one implementation, to calculate a dispersion parameter for a group of spectra, the intensity values (as a function of wavelength) are averaged together to provide an average spectrum. That is $I_{AVE}(\lambda)=(1/N)\cdot[\Sigma_{i=1 \text{ to } N} I_i(\lambda)]$, where N is the number of spectra in the group and $I_i(\lambda)$ are the spectra. For each spectrum in the group, a total difference between the spectrum and the average spectrum can then be calculated, e.g., using a sum of squares difference or sum of absolute values difference, e.g., $D_i=[1/(\lambda a-\lambda b)\cdot[\Sigma_{\lambda=\lambda a \text{ to } \lambda b} [I_i(\lambda)-I_{AVE}(\lambda)]^2]]^{1/2}$ or $D_i=[1/(\lambda a-\lambda b)\cdot[\Sigma_{\lambda=\lambda a \text{ to } \lambda b} |I_i(\lambda)-I_{AVE}(\lambda)|]]$ where $\lambda a$ to $\lambda b$ is the wavelength range being summed over.

Once a difference value has been calculated for each spectrum in the group of spectra, the value of the dispersion parameter can be calculated for the group from the difference values. A variety of dispersion parameters are possible, such as standard deviation, interquartile range, range (maximum value minus minimum value), mean difference, median absolute deviation and average absolute deviation. The sequence of dispersion values can be analyzed and used to detect clearance of the overlying layer (step 1408).

Figure 16:
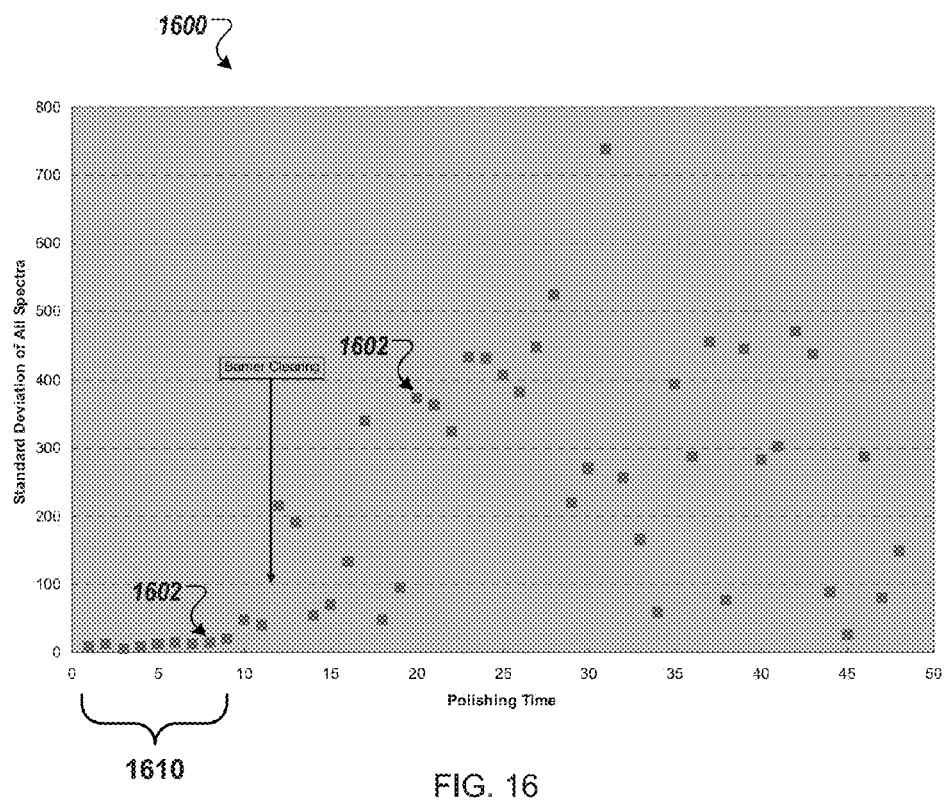
FIG. 16 shows a graph of standard deviation of spectra as a function of polishing time.

FIG. 16 shows a graph 1600 of the standard deviation of the spectra as a function of polishing time (with each standard deviation calculated from the difference values of a group of spectra). Thus, each plotted point 1602 in the graph is a standard deviation for the difference values of the group of spectra collected at a given sweep of the optical monitoring system. As illustrated, the standard deviation values remain fairly low during a first time period 1610. However, after time period 1610, the standard deviation values become larger and more disperse. Without being limited to any particular theory, a thick barrier layer may tend to dominate the reflected spectrum, masking differences in thickness of the barrier layer itself and any underlying layer. As polishing progresses, the barrier layer becomes thinner or is completely removed, and the reflected spectrum becomes more sensitive to variations in the underlying layer thickness. As a result, the dispersion of the spectra will tend to increase as the barrier layer is cleared.

A variety of algorithms can be used to detect the change in behavior of the dispersion values when the overlying layer is clearing. For example, the sequence of dispersion values can be compared to a threshold, and if a dispersion value exceeds the threshold, then a signal is generated indicating that the overlying layer has cleared. As another example, a slope of a portion of the sequence of dispersion values within a moving window can be calculated, and if the slope exceeds a threshold value then a signal is generated indicating that the overlying layer has cleared.

As part of the algorithm to detect the increase in dispersion, the sequence of dispersion values can be subject to a filter, e.g., a low-pass or band filter, in order to remove high frequency noise. Examples of low-pass filters include moving average and Butterworth filters.

Although the discussion above focuses on detection of clearance of a barrier layer, the technique can be used detection clearance of an overlying layer in other contexts, e.g., clearance of an overlying layer in another type semiconductor process that uses dielectric layer stacks, e.g., interlayer dielectric (ILD), or clearance of a thin metal layer over a dielectric layer.

In addition to use as trigger for initiating feature tracking as discussed above, this technique for detecting clearance of an overlying layer can be used for other purposes in a polishing operation, e.g., to be used as the endpoint signal itself, to trigger a timer so that the underlying layer is polished for a predetermined duration following exposure, or as a trigger to modify polishing parameter, e.g., to change carrier head pressure or slurry composition upon exposure of the underlying layer.

Figure 18:
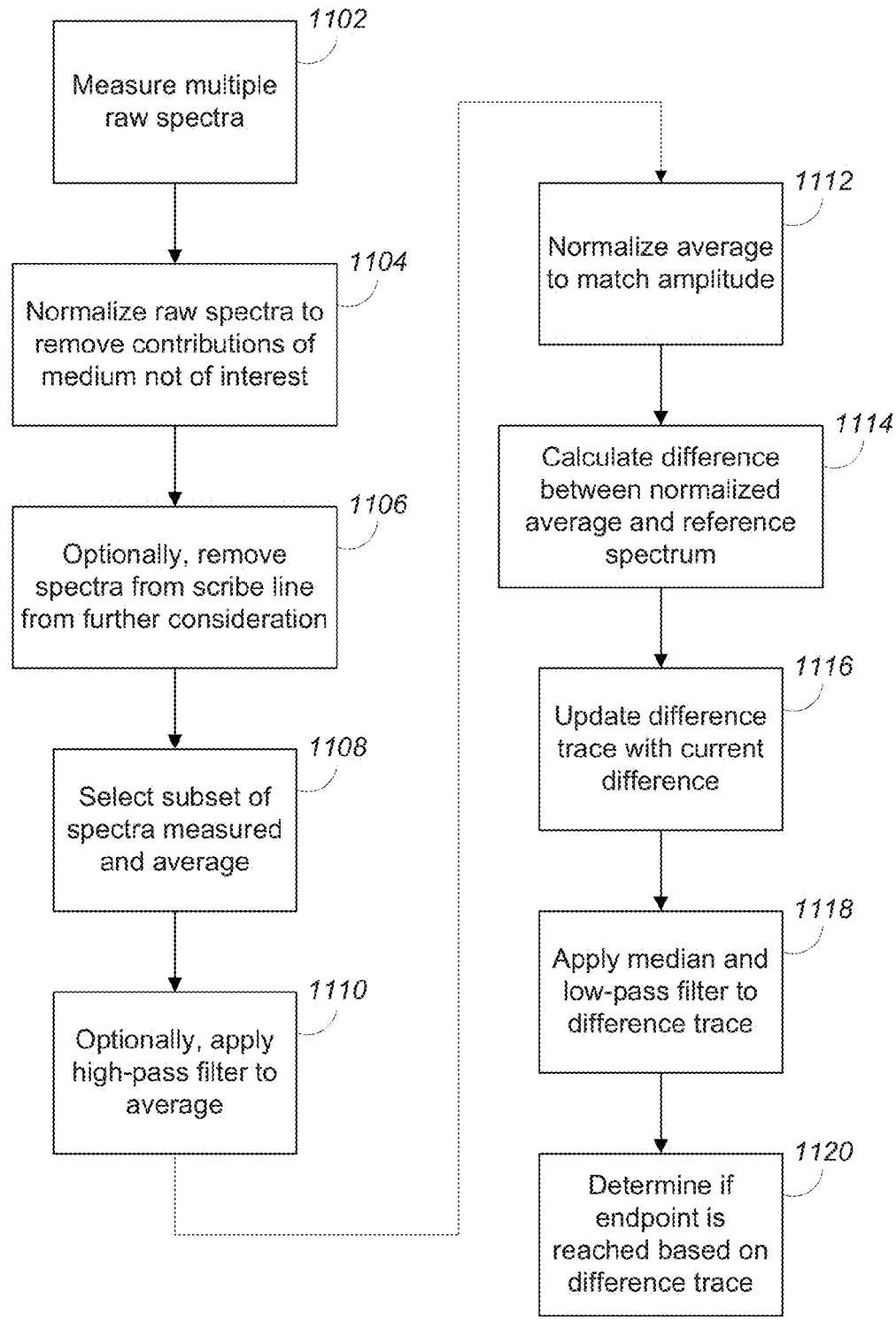
FIG. 18 shows an implementation for determining an endpoint.

FIG. 18 shows another implementation for determining an endpoint during a polishing step. For each platen revolution, the following steps are performed. One or more spectra of white light reflecting off a substrate surface being polished are measured (step 1102).

Each measured raw spectra is normalized (step 1104). Normalizing can remove light reflections contributed by mediums other than the film or films of interest. As discussed above, normalizing can include a division operation in which the raw spectrum is in the numerator and a base layer reference spectrum is in the denominator. In particular, a measured raw spectrum can be normalized as follows:

$$R=(A-D_A)/(B-D_B)$$

where R is the normalized spectrum, A is the raw spectrum, $D_A$ and $D_B$ are dark spectrums obtained under the dark condition, and B is the base layer reference spectrum. As discussed above, $D_A$ and $D_B$ can be the same spectrum, or $D_A$ and $D_B$ can be different spectra, e.g., $D_A$ is a dark spectrum collected when the raw spectrum is collected, e.g., at the same platen rotation, and $D_B$ is a dark spectrum collected when the base layer reference spectrum is collected, e.g., at the same platen rotation.

For each normalized spectrum, a difference value between the normalized spectrum and a reference spectrum is calculated, thus generating a sequence of difference values (step 1114). The difference is calculated using one of the above-described approaches, e.g., sum of square differences.

The sequence of difference values can be considered to provide a difference trace. The difference trace exhibits calculated differences between normalized averages and the reference spectrum as a function of time (or platen revolution).

A median and low-pass filter can be applied to the updated difference trace (step 1118). Application of these filters typically smoothes the trace (by reducing or eliminating spikes in the trace). A Savitzky-Golay filter can also be applied to smooth the trace.

Endpoint determination is performed based on the updated and filtered difference trace (step 1120). For example, polishing can be halted when the difference trace reaches a minimum, or when the difference trace falls below a threshold value.

Optionally, for either of the processes of FIG. 9 or FIG. 18, the measured spectra can be sorted based on the region of the pattern that has generated the spectrum, and spectra from some regions can be excluded from the endpoint calculation. In particular, spectra that are from light reflecting off scribe lines can be removed from consideration (e.g., step 1106). Different regions of a pattern substrate usually yield different spectra (even when the spectra were obtained at a same point of time during polishing). For example, a spectrum of the light reflecting off a scribe line in a substrate is different from the spectrum of the light reflecting off an array of the substrate. Because of their different shapes, use of spectra from both regions of the pattern usually introduces error into the endpoint determination. However, the spectra can be sorted based on their shapes into a group for scribe lines and a group for arrays. Because there is often greater variation in the spectra for scribe lines, usually these spectra can be excluded from consideration to enhance precision.

Optionally, for either of the processes of FIG. 9 or FIG. 18, if multiple spectra are measured in a single sweep of the sensor across the substrate, a subset of the spectra can be selected and averaged (e.g., step 1108). The subset consists of the spectra obtained from light reflecting off the substrate at points of a region on the substrate.

Optionally, for either of the processes of FIG. 9 or FIG. 18, a high-pass filter can be applied to the measured spectra, e.g., before or after normalization (e.g., step 1110). Application of the high pass filter can removes low frequency distortion of the average of the subset of spectra. The high-pass filter can be applied to the raw spectra, their average, or to both the raw spectra and their average.

The average is normalized so that its amplitude is the same or similar to the amplitude of the reference spectrum (step 1112). The amplitude of a spectrum is the peak-to-trough value of the spectrum. Alternatively, the average is normalized so that its reference spectrum is the same or similar to a reference amplitude to which the reference spectrum has also been normalized.

Figure 19:
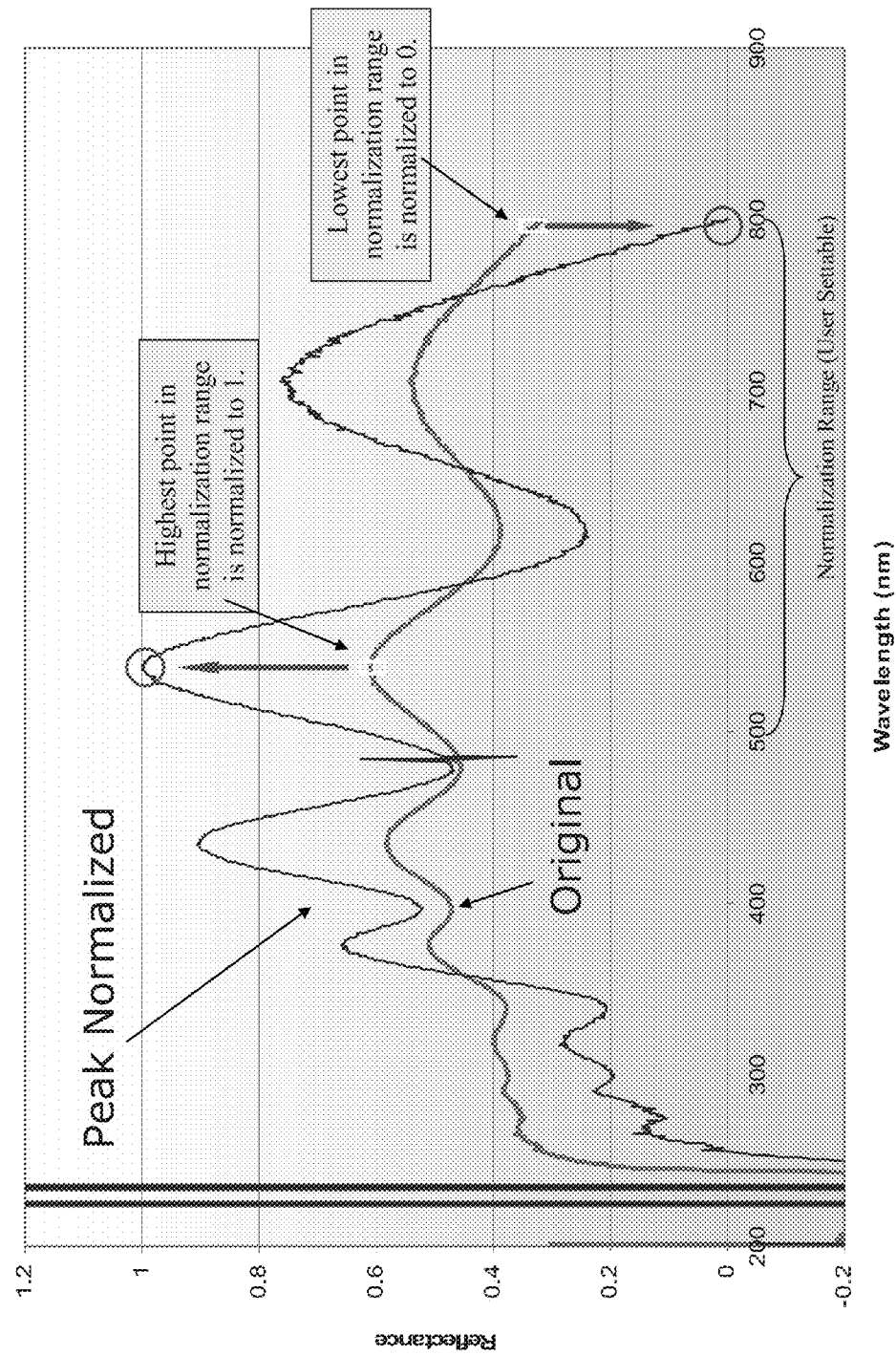
FIG. 19 is a graph showing normalization of a spectrum.

FIG. 19 illustrates the normalization of step 1112. As it can be seen, only a portion of a spectrum (or an average of spectra) is considered for normalization. The portion considered is referred to in the instant specification as a normalization range and, furthermore, can be user selectable. Normalization is effected so that the highest point and the lowest point in the normalization range are normalized to 1 and 0, respectively. The normalization is calculated as follows:

$$g=(1-0)/(r_{max}-r_{min})$$

$$h=1-r_{max}*g$$

$$N=R*g+h$$

where, g is a gain, h is an offset, $r_{max}$ is the highest value in the normalization range, $r_{min}$ is the lowest value in the normalization range, N is the normalized spectrum, and R is the pre normalized spectrum.

Although the discussion above assumes a rotating platen with an optical endpoint monitor installed in the platen, system could be applicable to other types of relative motion between the monitoring system and the substrate. For example, in some implementations, e.g., orbital motion, the light source traverses different positions on the substrate, but does not cross the edge of the substrate. In such cases, the collected spectra can still be grouped, e.g., spectra can be collected at a certain frequency and spectra collected within a time period can be considered part of a group. The time period should be sufficiently long that five to twenty spectra are collected for each group.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., the substrate can be a bare wafer, or it can include one or more deposited and/or patterned layers. The term substrate can include circular disks and rectangular sheets.

Embodiments of the invention and all of the functional operations described in this specification can be implemented in digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in a machine readable storage media, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network. The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

The above described polishing apparatus and methods can be applied in a variety of polishing systems. Either the polishing pad, or the carrier heads, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation.

Particular embodiments of the invention have been described. Other embodiments are within the scope of the following claims.

What is claimed is:

1. A computer program product for controlling polishing, the computer program product tangibly embodied in a non-transitory computer readable medium and comprising instructions to cause a processor to:
    receive from an in-situ optical monitoring system, during polishing of a substrate that includes a non-metallic first layer undergoing polishing, a semiconductor second layer, and a third layer between the non-metallic first layer and the semiconductor second layer, a sequence of raw spectra of light reflected from the substrate;
    store a reference spectrum, the reference spectrum being a spectrum of light reflected from a same material as the third layer;
    normalize each raw spectrum in the sequence of raw spectra to generate a sequence of normalized spectra, wherein the instructions to normalize include a division operation in which the raw spectrum is in the numerator and the reference spectrum is in the denominator; and
    determine at least one of a polishing endpoint or an adjustment for a polishing rate based on at least one normalized predetermined spectrum from the sequence of normalized spectra.

2. The computer program product of claim 1, further comprising instructions to store one or more dark spectra, the one or more dark spectra being measured by the in-situ optical monitoring system when no substrate is being measured by the in-situ optical monitoring system.

3. The computer program product of claim 2, wherein the instructions to normalize includes instructions to subtract the one or more dark spectra from the raw spectrum and the reference spectrum.

4. The computer program product of claim 3, wherein the instructions to normalize comprise instructions to calculate $$R = \frac{A - D_A}{B - D_B}$$

where R is the normalized spectrum, A is the raw spectrum, B is the reference spectrum and $D_A$ and $D_B$ are dark spectra.

5. The computer program product of claim 4, wherein $D_A$ and $D_B$ are the same dark spectrum.

6. The computer program product of claim 4, wherein $D_A$ and $D_B$ are different dark spectra.

7. The computer program product of claim 6, wherein $D_A$ is a dark spectrum collected when the raw spectrum is collected and $D_B$ is a dark spectrum collected when the reference spectrum is collected.

8. The computer program product of claim 6, wherein $D_A$ is a dark spectrum collected at the same platen rotation as the raw spectrum and $D_B$ is a dark spectrum collected at the same platen rotation as the reference spectrum.

9. The computer program product of claim 1, further comprising instructions to generate a sequence of values from the sequence of normalized spectra, fit a function to the sequence of values, determine a projected time at which the function reaches a target value, and determine at least one of the polishing endpoint or the adjustment for the polishing rate based on the projected time.

10. A method of controlling polishing, comprising:
    polishing a substrate that includes a non-metallic first layer undergoing polishing, a semiconductor second layer, and a third layer between the non-metallic first layer and the semiconductor second layer;
    measuring a sequence of raw spectra of light reflected from the substrate receive with an in-situ optical monitoring system;
    storing a reference spectrum, the reference spectrum being a spectrum of light reflected from a same material as the third layer;
    normalizing each raw spectrum in the sequence of raw spectra to generate a sequence of normalized spectra, wherein normalizing include a division operation in which the raw spectrum is in the numerator and the reference spectrum is in the denominator; and
    determining at least one of a polishing endpoint or an adjustment for a polishing rate based on at least one normalized predetermined spectrum from the sequence of normalized spectra.

11. The method of claim 10, further comprising instructions to store one or more dark spectra, the one or more dark spectra being measured by the in-situ optical monitoring system when no substrate is being measured by the in-situ optical monitoring system.

12. The method of claim 11, wherein the instructions to normalize includes instructions to subtract the one or more dark spectra from the raw spectrum and the reference spectrum.

13. The method of claim 12, wherein the instructions to normalize comprise instructions to calculate $$R = \frac{A - D_A}{B - D_B}$$

where R is the normalized spectrum, A is the raw spectrum, B is the reference spectrum and $D_A$ and $D_B$ are dark spectra.

14. The method of claim 13, wherein $D_A$ and $D_B$ are the same dark spectrum.

15. The method of claim 13, wherein $D_A$ and $D_B$ are different dark spectra.

16. The method of claim 15, wherein $D_A$ is a dark spectrum collected when the raw spectrum is collected and $D_B$ is a dark spectrum collected when the reference spectrum is collected.

17. The method of claim 15, wherein $D_A$ is a dark spectrum collected at the same platen rotation as the raw spectrum and $D_B$ is a dark spectrum collected at the same platen rotation as the reference spectrum.

18. The method of claim 10, further comprising generating a sequence of values from the sequence of normalized spectra, fitting a function to the sequence of values, determining a projected time at which the function reaches a target value, and determining at least one of the polishing endpoint or the adjustment for the polishing rate based on the projected time.

\* \* \* \* \*